United States Patent
Scharenberg et al.

(10) Patent No.: US 11,712,454 B2
(45) Date of Patent: Aug. 1, 2023

(54) METHOD FOR TREATING AUTOIMMUNE DISEASE USING CD4 T-CELLS WITH ENGINEERED STABILIZATION OF EXPRESSION OF ENDOGENOUS FOXP3 GENE

(71) Applicant: Seattle Children's Hospital, Seattle, WA (US)

(72) Inventors: Andrew M. Scharenberg, Seattle, WA (US); David J. Rawlings, Seattle, WA (US); Troy Torgerson, Bothell, WA (US)

(73) Assignee: SEATTLE CHILDREN'S HOSPITAL, Seattle, WA (US)

(*) Notice: Subject to any disclaimer, the term of this patent is extended or adjusted under 35 U.S.C. 154(b) by 961 days.

(21) Appl. No.: 16/345,622

(22) PCT Filed: Oct. 31, 2016

(86) PCT No.: PCT/US2016/059729
§ 371 (c)(1),
(2) Date: Apr. 26, 2019

(87) PCT Pub. No.: WO2018/080541
PCT Pub. Date: May 3, 2018

(65) Prior Publication Data
US 2019/0247443 A1    Aug. 15, 2019

(51) Int. Cl.
*A61K 35/545* (2015.01)
*C12N 15/85* (2006.01)
*C12N 15/10* (2006.01)
*C12N 15/66* (2006.01)
*A61K 48/00* (2006.01)
*A61P 37/06* (2006.01)
*A61K 38/20* (2006.01)
*C12N 5/0789* (2010.01)
*C12N 15/52* (2006.01)

(52) U.S. Cl.
CPC ........ *A61K 35/545* (2013.01); *A61K 38/2013* (2013.01); *A61K 48/00* (2013.01); *A61P 37/06* (2018.01); *C12N 5/0647* (2013.01); *C12N 15/102* (2013.01); *C12N 15/52* (2013.01); *C12N 15/66* (2013.01); *C12N 15/85* (2013.01)

(58) Field of Classification Search
CPC ....... C12N 9/22; C12N 15/85; C12N 2310/20
See application file for complete search history.

(56) References Cited

U.S. PATENT DOCUMENTS

| | | |
|---|---|---|
| 2015/0368611 A1 | 12/2015 | Seong |
| 2016/0184362 A1 | 6/2016 | Duchateau |
| 2016/0230188 A1 | 8/2016 | Rabinovch |
| 2019/0247443 A1 | 8/2019 | Scharenberg et al. |
| 2020/0123224 A1 | 4/2020 | Scharenberg |
| 2021/0054376 A1 | 2/2021 | Rawlings et al. |
| 2021/0253652 A1 | 8/2021 | Scharenberg |

FOREIGN PATENT DOCUMENTS

| | | | |
|---|---|---|---|
| EP | 1430124 B1 * | 11/2013 | ............. C12N 15/10 |
| WO | WO 02/090600 | 11/2002 | |
| WO | WO 08/009977 | 1/2008 | |
| WO | 2008095141 A3 † | 8/2008 | |
| WO | WO 08/095141 | 8/2008 | |
| WO | WO 09/067349 | 5/2009 | |
| WO | WO 2012/018930 A1 | 2/2012 | |
| WO | WO 14/180943 | 11/2014 | |
| WO | WO 14/191128 | 12/2014 | |
| WO | WO 15/140347 | 9/2015 | |
| WO | WO 2016/115179 A1 | 7/2016 | |
| WO | WO 16/123578 | 8/2016 | |
| WO | WO 2016/123578 A1 | 8/2016 | |
| WO | WO 17/186718 | 11/2017 | |
| WO | WO 18/031762 | 2/2018 | |
| WO | WO 18/073391 | 4/2018 | |
| WO | WO 18/081470 | 5/2018 | |
| WO | WO 18/205926 | 11/2018 | |
| WO | WO 19/040655 | 2/2019 | |
| WO | WO 19/241549 | 12/2019 | |

OTHER PUBLICATIONS

Fransson et al.; CAR/FoxP3-engineered T regulatory cells target the CNS and suppress EAE upon intranasal delivery; Journal of Neuroinflammation, 9:112, pp. 1-12, (2012)) (Year: 2012).*
Allan et al.; Generation of Potent and Stable Human CD4+ T Regulatory Cells by Activation-independent Expression of FOXP3; Molecular Therapy, vol. 16, No. 1, Jan. 2008, pp. 194-202 (Year: 2008).*
Fransson et al. 2012, CAR/FoxP3-engineered T regulatory cells target the CNS and suppress EAE upon intranasal delivery, Journal of Neuroinflammation, 9:112.
Hubbard, May 6, 2016, Nuclease-targeted gene-editing of FOXP3 in primary T cells creates a stable and functional $T_{reg}$ phenotype, PowerPoint presentation, 23 pp.
Schumann et al., Jul. 27, 2015, Generation of knock-in primary human T cells using Cas9 ribonucleoproteins, Proceedings of the National Academy of Sciences, 112(33):10437-10442.
International Search Report for PCT/US2016/059729 dated Mar. 9, 2017.

(Continued)

*Primary Examiner* — Antonio Galisteo Gonzalez
(74) *Attorney, Agent, or Firm* — Knobbe, Martens, Olson & Bear LLP

(57) ABSTRACT

Disclosed are methods of making a genetically cell that expressed FOXP3 and methods of treatment. In some embodiments, the method can providing a first nucleotide sequence, wherein the first nucleotide sequence comprises a coding strand, the coding strand comprising one or more regulatory elements and a FOXP3 gene or portion thereof providing a nuclease and performing a gene editing process on the first nucleotide sequence, which edits said one or more regulatory elements, and optionally edits the FOXP3 gene or portion thereof. Methods of treating a subject suffering from an autoimmune disease and subjects suffering the effects of organ transplantation are also provided.

19 Claims, 26 Drawing Sheets

(56) References Cited

OTHER PUBLICATIONS

Allan et al., Jan. 2008, Generation of potent and stable human CD4+ T regulatory cells by activation-independent expression of FOXP3, Mol Ther. 16(1):194-202.

Baron et al., 2007, DNA demethylation in the human FPXP3 locus discriminates regulatory T cells from activate FPXP3+ conventional T cells, Eur J Immunol. 37(9):2378-89.

Bettini et al., May 25, 2012, Loss of epigenetic modification driven by the Foxp3 transcription factor leads to regulator T cell insufficiency, Immunity, 36(5):717-730.

Challita et al., Feb. 1995, Multiple modifications in cis elements of the long terminal repeat of retroviral vectors lead to increased expression and decreased DNA methylation in embryonic carcinoma cells, J. Virol. 69(2):748-755.

Darce et al., May 25, 2012, An N-terminal mutation of the Foxp3 transcription factor alleviates arthritis but exacerbates diabetes, Immunity. 36(5):731-741.

Engels et al., Aug. 10, 2003, Retroviral Vectors for High-Level Transgene Expression in T Lymphocytes, Human Gene Therapy, 14:1155-1168.

Fantini et al., 2004, Cutting edge: TGF-β induces a regulatory phenotype in CD4+CD25- T cells through Foxp3 induction and down-regulation of Smad7, J Immunol. 172(9):5149-5153.

Fontenot et al., Apr. 2003, Foxp3 programs the development and function of CD4+CD25+ regulatory T cells, Nat Immunol. 4(4):330-336.

Ghali et al., 2017, Induced regulatory T cells are phenotypically unstable and do not protect mice from rapidly progressive glomerulopephritis, Immunology. 150(1):100-114.

Honaker et al., 2020, Gene editing to induce FOXP3 expression in human CD4+ T cells leads to a stable regulatory phenotype and function, Sci Transl Med. 12(546):eaay6422, 18 pp.

Hori et al., Feb. 14, 2003, Control of regulatory T cell development by the transcription factor Foxp3, Science. 299(5609):1057-1061.

Hubbard et al. May 1, 2016, Nuclease-targeted gene-editing of FOXP3 in primary T cells creates a stable and functional T phenotype, Mol Ther. 24(Suppl. 1):S18 (ASGCT Abstract).

Konya et al., 2013, T Cells as Treatment Targets in Systemic Lupus Erythematosus, Rheumatology: Current Research, 3(2), pp. 3 pages.

Loser et al., 2005, In vitro-generated regulatory T cells induced by Foxp3-retrovirus infection control murine contact allergy and systemic autoimmunity, Gene Ther. 12(17):1294-1304.

Okada et al., 2017, Stabilization of Foxp3 expression by CRISPR-dCas9-based epigenome editing in mouse primary T cells, Epigenetics Chromatin. 10:24.

Passerini et al., Dec. 11, 2013, CD4+ T cells from IPEX patients convert into functional and stable regulatory T cells by FOXP3 gene transfer, Sci Transl Med. 5(215):215ra174.

Qin et al., May 2010, Systematic Comparison of Constitutive Promoters and the Doxycycline-Inducible Promoter, PLOS One, 5(5):el 0611-1-el 0611-4.

Schubert et al., 2001, Scurfin (FOXP3) acts as a repressor of transcription and regulates T cell activation, J Biol Chem. 276(40):37672-37679.

Wright et al. Nov. 10, 2009, Adoptive therapy with redirected primary regulatory T cells results in antigen-specific suppression of arthritis, PNAS 106(45):19078-19083.

Fransson M., et al., "CAR/FoxP3-engineered T regulatory cells target the CNS and suppress EAE upon intranasal delivery," Journal of Neuroinflammation, vol. 9, Issue No. 112, 12 pages (2012).†

Wright G.P., et al., "Adoptive therapy with redirected primary regulatory T cells results in antigen-specific suppression of arthritis," Proceedings of the National Academy of Sciences of the United States of America, vol. 106, Issue No. 45, pp. 19078-19083 (Nov. 2009).†

Engels B., et al., "Retroviral Vectors for High-Level Transgene Expression in T Lymphocytes," Human Gene Therapy, vol. 14, pp. 1155-1168 (Aug. 2003).†

Allan S.E., et al., "Generation of Potent and Stable Human CD4+ T Regulatory Cells by Activation-independent Expression of FOXP3," Molecular Therapy, vol. 16, Issue No. 1, pp. 194-202 (Jan. 2008).†

Riley J.L., et al., "Human T Regulatory Cells as Therapeutic Agents: Take a Billion or So of These and Call Me in the Morning," Immunity, vol. 30, Issue No. 5, pp. 656-665 (May 2009).†

Konya C., et al., "T Cells as Treatment Targets in Systemic Lupus Erythematosus," Rheumatology: Current Research, vol. 3, Issue No. 2, pp. 3 pages (2013).†

Qin et al., "Systematic Comparison of Constitutive Promoters and the Doxycycline-Inducible Promoter," PLOS One, vol. 5, Issue No. 5, pp. e10611-1-e10611-4 (May 2010).†

* cited by examiner
† cited by third party

METHOD FOR TREATING AUTOIMMUNE DISEASE USING CD4 T-CELLS WITH ENGINEERED STABILIZATION OF EXPRESSION OF ENDOGENOUS FOXP3 GENE

CROSS REFERENCE TO RELATED APPLICATIONS

This application is a U.S. National Phase Application of PCT International Application Number PCT/US2016/059729, filed on Oct. 31, 2016, designating the United States of America and published in the English language. The disclosures of the above-referenced applications are hereby expressly incorporated by reference in their entireties.

FIELD OF THE INVENTION

Described herein are methods for therapy of auto-immune disease and for induction of tolerance to transplanted organs. The methods can also be used for cellular therapy for severe auto-immune disease and organ transplantation.

BACKGROUND OF THE INVENTION

Immunological self-tolerance in the periphery can be achieved by negative regulation that can be exerted on the immune response by a variety of cells of which the best characterized populations are the regulatory T cells ($T_{regs}$). $T_{regs}$ mediate self-tolerance and tolerance to alloantigens by suppressing the activation of effector T-cells ($T_{effs}$), and exerting anti-inflammatory activity. CD4+CD25+Foxp3+ $T_{regs}$, are one of the best studied and characterized T cells, in the context of autoimmune diseases and organ transplantation, for example.

$T_{regs}$ have also been known as "suppressor T cells." It was also described that specifically, CD4+, CD25+ regulatory T cells can exhibit regulatory functions in vitro and in vivo and that they suppress the proliferation of CD4+ and CD8+ $T_{effs}$ in vitro. These cells were also shown to play an important role in autoimmunity, allergy, inflammation, and maintenance of maternal tolerance to a fetus, infections and cancer. $T_{regs}$ have been known to turn the immune response down. In cancer, an excess of $T_{regs}$ cell activity can prevent the immune system from destroying cancer cells. In autoimmune disease, a deficiency of regulatory T cell activity can allow other autoimmune cells to attack the body's own tissues.

The $T_{regs}$ cells can also include natural (n) $T_{regs}$ that are generated in the thymus and inducible (i$T_{regs}$) that are generated in the periphery. The n$T_{regs}$ arise in the thymus and can express the forkhead/winged helix transcription factor FOXP3 that, in turn, controls nTreg differentiation. i$T_{regs}$ arise in the periphery from memory and naive CD4+ $T_{effs}$ following stimulation by self- or allo-antigens in the presence of IL-4, IL-10, TGF-β and IL-2.

FOXP3 is a protein involved in immune system responses and is encoded by FOXP3 genes containing 11 coding exons, with the first coding exon designated exon 2 in a revised nomenclature. FOXP3, has been characterized as a master regulator of the regulatory pathway in the development and function of regulatory T cells. In animal studies it has been shown that $T_{regs}$ that express FOXP3, are crucial in the transfer of immune tolerance, such as self-tolerance. Furthermore induction or administration of FOXP3 positive cells have been shown to lead to reductions in autoimmune disease severity in models of diabetes, multiple sclerosis, asthma, inflammatory bowel disease, thyroiditis and renal disease.

The use of $T_{regs}$ for treatment of disease or for the suppression of the immune system in the event of organ transplantation has previously been proposed. However, one of the most important barriers to the use of either t$T_{regs}$ or p$T_{regs}$ for therapy of autoimmune disease is that FOXP3 expression is subject to epigenetic regulation. In t$T_{regs}$, an upstream region in the FOXP3 gene known as the "thymus specific demethylated region" is completely demethylated, a state that is thought to result in stable FOXP3 expression. Generally, full demethylation is not observed in p$T_{regs}$. Under inflammatory conditions, FOXP3 may be silenced epigenetically in p$T_{regs}$, and possibly t$T_{regs}$ (although some investigators believe that t$T_{regs}$ are completely stable), which can potentially result in conversion of p$T_{regs}$ to pro-inflammatory CD4+ T-cells. The lack of stability of p$T_{regs}$ is a significant concern, as the use of infusion of p$T_{regs}$ that revert to an inflammatory phenotype could result in a worsening of auto-immune symptoms. As such, a safe method for the induction of FOXP3 in $T_{regs}$ is needed.

SUMMARY OF THE INVENTION

Many groups are interested in treating auto-immune diseases with regulatory T-cells, due to the possibility for these cells to induce antigen specific tolerance. There are many forms of regulatory T-cells ("$T_{regs}$"), with current nomenclature dividing $T_{regs}$ into those which are generated in the thymus in the course of T-cell development, denoted as thymic regulatory T-cells or "t$T_{regs}$", and peripherally induced regulatory T-cells, denoted as peripheral regulatory T-cells or "p$T_{regs}$".

A key aspect of regulatory T-cell biology is the expression of the transcription factor FOXP3. FOXP3 is thought to be required to specify the regulatory T-cell lineage. This concept is based on the observation that humans who lack FOXP3 develop severe autoimmune disease starting in the neonatal period. However, the most important barriers to the use of either t$T_{regs}$ or p$T_{regs}$ for therapy of autoimmune disease are that FOXP3 expression is subject to epigenetic regulation. In t$T_{regs}$, an upstream region in the FOXP3 gene known as the "thymus specific demethylated region" is completely demethylated, a state which is thought to result in stable FOXP3 expression. Generally, full demethylation is not observed in p$T_{regs}$. Under inflammatory conditions, FOXP3 may be silenced epigenetically in p$T_{regs}$, and possibly t$T_{regs}$. This can result in conversion of p$T_{regs}$ to pro-inflammatory CD4 T-cells. The lack of stability of p$T_{regs}$ is a significant concern, as the use of infusion of pTregs that revert to an inflammatory phenotype could result in a worsening of auto-immune symptoms.

The proposed method of enforcing FOXP3 expression in a bulk population of CD4 T cells is an improvement over other approaches to isolating native regulatory T-cell populations as it provides the ability to capture the TCR repertoire present in the inflammatory T-cell population. In patients with auto-immune disease or who are rejecting an organ graft, the endogenous TCR repertoire in the inflammatory T-cell population includes TCR's that have the correct binding specificity to recognize the inflamed tissue or the foreign tissue in the organ. These T-cells are thought to mediate the auto-inflammatory reaction or organ rejection. By converting a portion of the bulk CD4 T-cell population to a regulatory phenotype, the TCR specificities present in the pro-inflammatory population will be represented in the therapeutic cell population. This is an improvement over therapies based on thymic regulatory T-cells, which is thought to have a distinct and non-overlapping TCR repertoire from inflammatory T-cells. In addition, presumably in patients with auto-immune disease or organ rejection, the existing tTreg population has failed to produce the tolerance necessary to avoid inflammation.

Accordingly, several aspects of the invention described herein concern methods for the treatment or amelioration of auto-immune diseases using CD4 T-cells that have been engineered to have stable expression of their endogenous FOXP3 gene. Several approaches described herein utilize an engineering approach, for example, which stabilizes FOXP3 expression in CD4 T-cells and allows for the generation of expanded populations of potentially suppressive T-cells that are no longer susceptible to epigenetic modification of their suppressive function. As a result, such cells will have improved properties for therapeutic application.

In a first aspect, a method of making a nucleic acid for expression of FOXP3 is provided, wherein the method comprises providing a first nucleotide sequence, wherein the first nucleotide sequence comprises a coding strand, the coding strand comprising one or more regulatory elements and a FOXP3 gene or portion thereof, providing a nuclease and performing a gene editing process on the first nucleotide sequence, which edits said one or more regulatory elements, and optionally edits the FOXP3 gene or portion thereof. In some alternatives, the first nucleotide sequence comprises a targeted locus. In some alternatives, the targeted locus comprises a natural first coding exon. In some alternatives, completion of the gene editing process results in a first coding exon in the targeting locus following the gene editing process. In some alternatives, the targeted locus is at the one or more regulatory elements. In some alternatives, the targeted locus is at the FOXP3 gene or portion thereof. In some alternatives, the FOXP3 gene or portion thereof comprises the first natural coding exon. In some alternatives, the nuclease is Cas9, a zinc-finger nuclease or TALEN. In some alternatives, the gene editing process is a gene knock-in process for insertion of a heterologous promoter, a heterologous transcriptional enhancer domain or both. In some alternatives, the heterologous promoter is a constitutive promoter. In some alternatives, the promoter is an EF1 alpha promoter, a PGK promoter, or an MND promoter. In some alternatives, the promoter is a heterologous weak promoter (e.g., a promoter that generates less expression than the endogenous promoter and/or a constitutive promoter). In some alternatives, the promoter is an inducible promoter. In some alternatives, the inducible promoter is inducible by a drug or a steroid. In some alternatives, the method further comprises insertion of a heterologous transcriptional enhancer domain, wherein the enhancer domain is upstream or downstream from the one or more regulatory sequences. In some alternatives, the method further comprises insertion of a heterologous transcriptional activation domain. In some alternatives, the method further comprises insertion of a ubiquitous chromatin opening element (UCOE). In some alternatives, the method further comprises insertion of an inducible effector. In some alternatives, the inducible effector is inducible by a steroid or a drug. In some alternatives, the heterologous promoter is inserted, wherein insertion of the heterologous promoter generates the first coding exon wherein the heterologous promoter is at a position anywhere upstream from the first coding exon on the coding strand, and wherein the coding strand further comprises a start codon of the FOXP3 gene. In some alternatives, the heterologous promoter is inserted at a position anywhere upstream from the first natural exon on the coding strand, and wherein the coding strand further comprises a start codon of the FOXP3 gene. In some alternatives, the heterologous promoter is inserted downstream from the one or more regulatory elements on the coding strand. In some alternatives, the method further comprises genetically modifying the one or more regulatory elements.

In a second aspect, a nucleic acid for FOXP3 expression, made by any one of the methods of any one of the alternatives herein is provided. The method comprises providing a first nucleotide sequence, wherein the first nucleotide sequence comprises a coding strand, the coding strand comprising one or more regulatory elements and a FOXP3 gene or portion thereof, providing a nuclease and performing a gene editing process on the first nucleotide sequence, which edits said one or more regulatory elements, and optionally edits the FOXP3 gene or portion thereof. In some alternatives, the first nucleotide sequence comprises a targeted locus. In some alternatives, the targeted locus comprises a natural first coding exon. In some alternatives, completion of the gene editing process results in a first coding exon in the targeting locus following the gene editing process. In some alternatives, the targeted locus is at the one or more regulatory elements. In some alternatives, the targeted locus is at the FOXP3 gene or portion thereof. In some alternatives, the FOXP3 gene or portion thereof comprises the first natural coding exon. In some alternatives, the nuclease is Cas9, a zinc-finger nuclease or TALEN. In some alternatives, the gene editing process is a gene knock-in process for insertion of a heterologous promoter, a heterologous transcriptional enhancer domain or both. In some alternatives, the heterologous promoter is a constitutive promoter. In some alternatives, the promoter is an EF1 alpha promoter, a PGK promoter, or an MND promoter. In some alternatives, the promoter is a heterologous weak promoter (e.g., a promoter that generates less expression than the endogenous promoter and/or a constitutive promoter). In some alternatives, the promoter is an inducible promoter. In some alternatives, the inducible promoter is inducible by a drug or a steroid. In some alternatives, the method further comprises insertion of a heterologous transcriptional enhancer domain, wherein the enhancer domain is upstream or downstream from the one or more regulatory sequences. In some alternatives, the method further comprises insertion of a heterologous transcriptional activation domain. In some alternatives, the method further comprises insertion of a ubiquitous chromatin opening element (UCOE). In some alternatives, the method further comprises insertion of an inducible effector. In some alternatives, the inducible effector is inducible by a steroid or a drug. In some alternatives, the heterologous promoter is inserted, wherein insertion of the heterologous promoter generates the first coding exon wherein the heterologous promoter is at a position anywhere upstream from the first coding exon on the coding strand, and wherein the coding strand further comprises a start codon of the FOXP3 gene. In some alternatives, the heterologous promoter is inserted at a position anywhere upstream from the first natural exon on the coding strand, and wherein the coding strand further comprises a start codon of the FOXP3 gene. In some alternatives, the heterologous promoter is inserted downstream from the one or more regulatory elements on the coding strand. In some alternatives, the method further comprises genetically modifying the one or more regulatory elements.

In a third aspect, a nucleic acid is provided, the nucleic acid comprising a coding strand that comprises heterologous regulatory elements and a heterologous promoter, which are operably linked to a FOXP3 gene or portion thereof, wherein the FOXP3 gene or portion thereof comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the promoter is an inducible promoter. In some alternatives, the inducible promoter is inducible by a drug or a steroid. In some alternatives, the heterologous promoter is at a position upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified.

In a fourth aspect, a method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In a fifth aspect, a genetically engineered cell for the expression of FOXP3, manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In a sixth aspect, a genetically engineered cell for the expression of FOXP3, the genetically engineered cell comprising a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In a seventh aspect, a composition comprising the genetically engineered cell of any one or more of the cells of any one of the alternatives herein and a pharmaceutical excipient is provided. The genetically engineered cell for the expression of FOXP3 can be manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the genetically engineered cell for the expression of FOXP3 comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In an eighth aspect, a method of treating, inhibiting, or ameliorating an autoimmune disorder in a subject, the method comprising: administering to the subject the genetically modified cell of any one of more of the cells of any one of the alternatives herein or the composition of any one of the alternatives is provided. The composition comprising the genetically engineered cell of any one or more of the cells of any one of the alternatives herein and a pharmaceutical excipient is provided. The genetically engineered cell for the expression of FOXP3 can be manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the genetically engineered cell for the expression of FOXP3 comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the autoimmune disease is rheumatoid arthritis, diabetes, inflammatory bowel disease, IPEX, immune dysregulation, polyendocrinopathy, enteropathy, X-linked (IPEX) syndrome, Crohn's disease, multiple sclerosis, idiopathic or systemic lupus erythematosus. In some alternatives, the subject is identified or selected to receive therapy for an autoimmune disease.

In a ninth aspect, a method of treating, inhibiting, or ameliorating side effects of organ transplantation in a subject is provided, the method comprising: administering to the subject the genetically modified cell of any one of more of the cells of any one of the alternatives herein or the composition of any one of the alternatives is provided. The composition comprising the genetically engineered cell of any one or more of the cells of any one of the alternatives herein and a pharmaceutical excipient is provided. The genetically engineered cell for the expression of FOXP3 can be manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the genetically engineered cell for the expression of FOXP3 comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In a tenth aspect, a method of treating, inhibiting, or ameliorating side effects of organ transplantation in a subject, such as organ rejection is provided, the method comprising: administering to the subject the genetically modified cell of any one of more of the cells of any one of the alternatives herein or the composition of any one of the alternatives is provided. The composition comprising the genetically engineered cell of any one or more of the cells of any one of the alternatives herein and a pharmaceutical excipient is provided. The genetically engineered cell for the expression of FOXP3 can be manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the genetically engineered cell for the expression of FOXP3 comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In an eleventh aspect, a method of treating, inhibiting, or ameliorating an autoimmune disorder in a subject is provided, the method comprising withdrawing cells from the subject in need, wherein the cells comprise a first nucleotide sequence, wherein the first nucleotide sequence comprises a coding strand, the coding strand comprising one or more regulatory elements, a FOXP3 gene or portion thereof, wherein the FOXP3 gene or portion thereof comprises a first coding exon, providing a second nucleotide sequence encoding a nuclease or providing a protein nuclease, introducing the second nucleotide sequence or protein nuclease into the cell for genetic modification, wherein the genetic modification is a gene knock-in process for insertion of a promoter into the first nucleotide sequence; and introducing the cell into the subject for treatment, inhibition, or amelioration. In some alternatives, the autoimmune disease is rheumatoid arthritis, diabetes, inflammatory bowel disease, IPEX, immune dysregulation, polyendocrinopathy, enteropathy, X-linked (IPEX) syndrome, Crohn's disease, multiple sclerosis, idiopathic or systemic lupus erythematosus. In some alternatives, the subject is identified or selected to receive therapy for an autoimmune disease. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In a twelfth aspect, a method of treating, inhibiting, or ameliorating side effects of organ transplantation in a subject is provided, the method comprising withdrawing cells from the subject in need, wherein the cells comprise a first nucleotide sequence, wherein the first nucleotide sequence comprises a coding strand, the coding strand comprising one or more regulatory elements, a FOXP3 gene or portion thereof, wherein the FOXP3 gene or portion thereof comprises a first coding exon, providing a second nucleotide sequence encoding a nuclease or providing a protein nuclease, introducing the second nucleotide sequence or protein nuclease into the cell for genetic modification, wherein the genetic modification is a gene knock-in process for insertion of a promoter into the first nucleotide sequence; and introducing the cell into the subject for treatment, inhibition, or amelioration. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In a thirteenth aspect, a method of treating, inhibiting, or ameliorating side effects of organ transplantation in a subject, such as organ rejection is provided, the method comprising withdrawing cells from the subject in need, wherein the cells comprise a first nucleotide sequence, wherein the first nucleotide sequence comprises a coding strand, the coding strand comprising one or more regulatory elements, a FOXP3 gene or portion thereof, wherein the FOXP3 gene or portion thereof comprises a first coding exon, providing a second nucleotide sequence encoding a nuclease or providing a protein nuclease, introducing the second nucleotide sequence or protein nuclease into the cell for genetic modification, wherein the genetic modification is a gene knock-in process for insertion of a promoter into the first nucleotide sequence and introducing the cell into the subject for treatment, inhibition or amelioration. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

DETAILED DESCRIPTION OF THE PREFERRED EMBODIMENT

Described herein, are several methods of treatment or amelioration of auto-immune diseases using CD4 T-cells that have been engineered to have stable expression of their endogenous FOXP3 gene. These methods can also be used to ameliorate the effects of graft versus host disease (GVHD).

Definitions

As used herein, "nucleic acid" or "nucleic acid molecule" refers to polynucleotides or oligonucleotides such as deoxyribonucleic acid (DNA) or ribonucleic acid (RNA), oligonucleotides, fragments generated by the polymerase chain reaction (PCR), and fragments generated by any of ligation, scission, endonuclease action, exonuclease action, and by synthetic generation. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate. The term "nucleic acid molecule" also includes so-called "peptide nucleic acids," which comprise naturally-occurring or modified nucleic acid bases attached to a polyamide backbone. Nucleic acids can be either single stranded or double stranded.

"Coding strand" as described herein, is the DNA strand which has the same base sequence as the RNA transcript produced (although with thymine replaced by uracil). It is this strand, which contains codons, while the non-coding strand contains anti-codons.

"Regulatory elements" as described herein, refers to a segment of a nucleic acid molecule, which is capable of increasing or decreasing the expression of specific genes within an organism. Regulation of gene expression is an essential feature of all living organisms and viruses. Without being limiting, examples of regulatory elements can include, CAAT box, CCAAT box, Pribnow box, TATA box, SECIS element, mRNA Polyadenylation signals, A-box, Z-box, C-box, E-box, G-box, hormone responsive elements, such as insulin gene regulatory sequences, DNA binding domains, activation domains, and/or enhancer domains.

Figure 1:
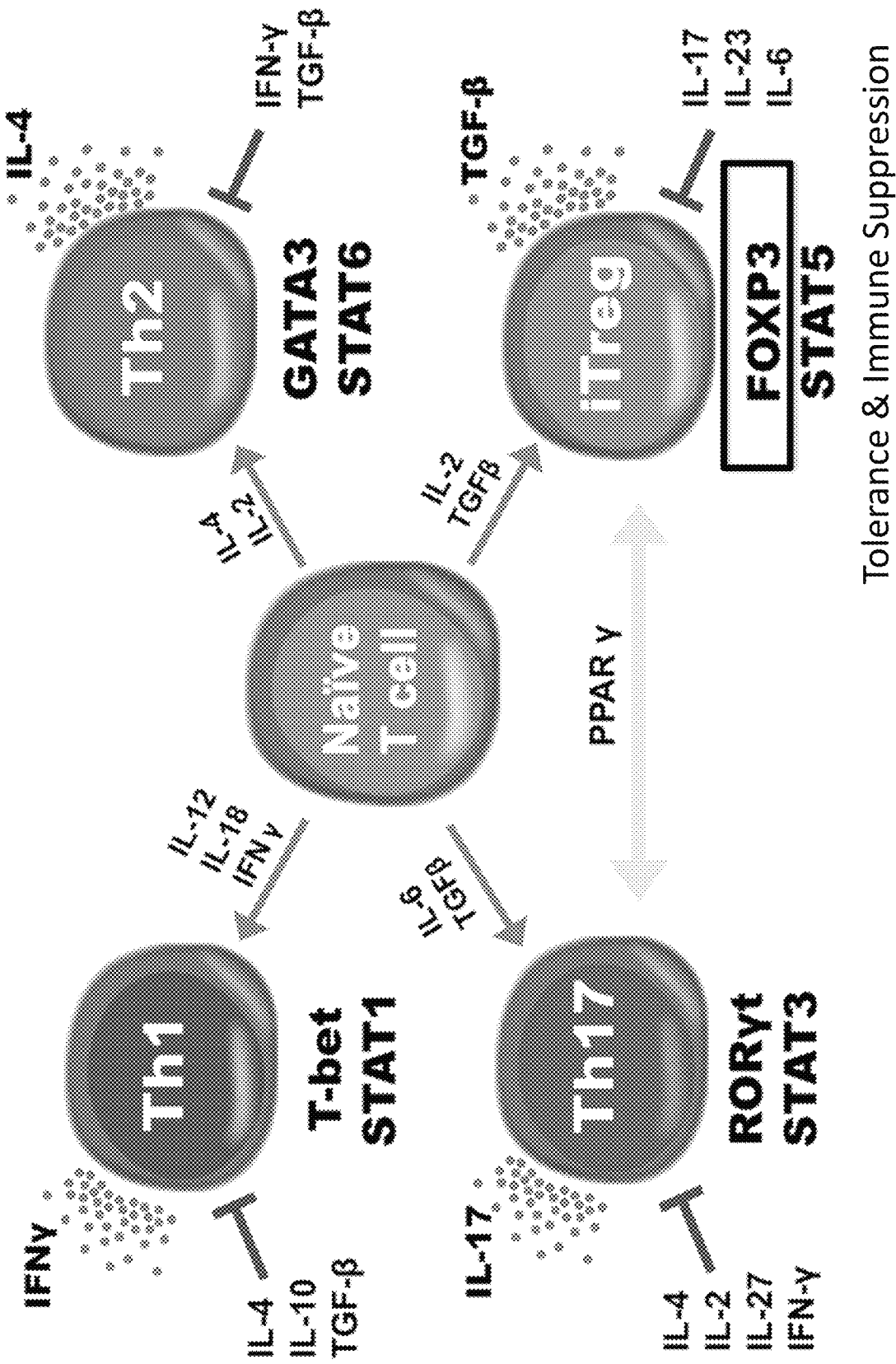
FIG. 1: FOXP3 promotes the $T_{reg}$ lineage. As shown in the Figure the Naïve T cell expresses IL-12, IL-18, IFNγ, IL-6, TGF-β, IL-4 and IL-2, which in turn regulates TH1, TH17, TH2, and iTregs. The $T_{regs}$ play a critical role in multiple autoimmune diseases (IPEX, T1D, SLE, RA, EAE, etc). Approaches to augment human Treg number or function are in current trials including low-dose IL-2 and adoptive transfer of autologous expanded Treg. The efficacy of IL-2 therapy is limited due to its pleotropic activity and potential "off target" effects that may increase inflammation. Adoptive Treg therapy is likely limited by in vivo stability and viability of expanded Tregs and their lack of relevant antigen specificity.

"FOXP3" as described herein, is a protein that is involved in immune system responses. The FOXP3 gene contains 11 coding exons. Foxp3 is a specific marker of natural T regulatory cells ($nT_{regs}$, a lineage of T cells) and adaptive/induced T regulatory cells ($a/iT_{regs}$). Induction or administration of Foxp3 positive T cells has, in animal studies, was shown to lead to marked reductions in (autoimmune) disease severity in models of diabetes, multiple sclerosis, asthma, inflammatory bowel disease, thyroiditis and renal disease. However, T cells have been able to show plasticity in studies. Thus, the use of regulatory T cells in therapy can be risky, as the T regulatory cell transferred to the patient may change into T helper 17 (Th17) cells, which are pro-inflammatory rather than regulatory cells. As such, methods are provided herein to avoid the risks that may arise from regulatory cells changing into pro-inflammatory cells. As shown in FIG. 1, FOXP3 expressed from an iTreg is used as a master regulator of the immune system and is used for tolerance and immune suppression. Treg play a critical role in multiple autoimmune diseases (IPEX, T1D, SLE, RA, EAE, etc). Approaches to augment human Treg number or function are in current trials including low-dose IL-2 and adoptive transfer of autologous expanded Treg. The efficacy of IL-2 therapy is limited due to its pleotropic activity and potential "off target" effects that may increase inflammation. Adoptive Treg therapy is likely limited by in vivo stability and viability of expanded $T_{regs}$ and their lack of relevant antigen specificity.

"Nuclease" as described herein, is a protein or an enzyme capable of cleaving the phosphodiester bonds between the nucleotide subunits of nucleic acids. The nuclease described herein, is used for "gene editing" which is a type of genetic engineering in which DNA is inserted, deleted or replaced in the genome of a living organism using a nuclease or an engineered nuclease or nucleases. Without being limiting, the nuclease can be of the CRISPR/CAS9 system, a zinc finger nuclease or TALEN nuclease. The nuclease can be used to target a locus, or a targeted locus on a nucleic acid sequence.

"Coding exon" as described herein, refers to any part of a gene that will encode a part of the final mature RNA produced by that gene after introns have been removed by RNA splicing. The term exon refers to both the DNA sequence within a gene and to the corresponding sequence in RNA transcripts. In RNA splicing, introns are removed and exons are covalently joined to one another as part of generating the mature messenger RNA.

"Cas9" as described herein, is an RNA-guided DNA endonuclease enzyme associated with the CRISPR (Clustered Regularly Interspaced Short Palindromic Repeats) adaptive immunity system.

"Zinc finger nuclease" as described herein, is an artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes.

"TALEN" or "Transcription activator-like effector nuclease" as described herein, is restriction enzymes that can be engineered to cut specific sequences of DNA. They are made by fusing a TAL effector DNA-binding domain to a DNA cleavage domain (a nuclease which cuts DNA strands). Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ, a technique known as genome editing with engineered nucleases. Alongside zinc finger nucleases and CRISPR/Cas9, TALEN is a prominent tool in the field of genome editing.

"Knock-in" as described herein, refers to a genetic engineering method that involves the one-for-one substitution of DNA sequence information with a wild-type copy in a genetic locus or the insertion of sequence information not found within the locus.

A "promoter" is a nucleotide sequence that directs the transcription of a structural gene. In some alternatives, a promoter is located in the 5' non-coding region of a gene, proximal to the transcriptional start site of a structural gene. Sequence elements within promoters that function in the initiation of transcription are often characterized by consensus nucleotide sequences. It is a region of DNA that initiates transcription of a particular gene. Promoters are located near the transcription start sites of genes, on the same strand and upstream on the DNA (towards the 5' region of the sense strand). Promoters can be about 100, 200, 300, 400, 500, 600, 700, 800, or 1000 base pairs long or within a range defined by any two of the aforementioned lengths. As used herein, a promoter can be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known. Without being limiting, examples of promoters can include a constitutive promoter, a heterologous weak promoter (e.g., a promoter that generates less expression than the endogenous promoter and/or a constitutive promoter) or inducible promoters. Examples can include EF1 alpha promoter, a PGK promoter, an MND promoter, KI promoter, Ki-67 gene promoter, and/or a promoter inducible by a drug such as tamoxifen and/or its metabolites. Commonly used constitutive promoters can include but are not limited to SV40, CMV, UBC, EF1A, PGK, and/or CAGG for mammalian systems.

A weak promoter produces less mRNA expression than a stronger promoter, if both are driving expression of the same coding sequences. This can be compared by analyzing, for example, an agarose gel. An example of promoters subject to regulation by proximal chromatin is the EF1 alpha short promoter, which is highly active in some loci, but nearly inactive in other loci (Eyquem, Biotechnol Bioeng. 2013 August; 110(8):2225-35. doi: 10.1002/bit. 24892.)

"Transcriptional enhancer domain" as described herein, refers to a short (50-1500 bp) region of DNA that can be bound by proteins (activators) to increase or promote or enhance the likelihood that transcription of a particular gene will occur or the level of transcription that takes place. These activator proteins are usually referred to as transcription factors. Enhancers are generally cis-acting, located up to 1 Mbp (1,000,000 bp) away from the gene and can be upstream or downstream from the start site, and either in the forward or backward direction. An enhancer may be located upstream or downstream of the gene it regulates. A plurality of enhancer domains may be used in some embodiments to generate greater transcription e.g., multimerized activation binding domains can be used to further enhance or increase the level of transcription. Furthermore, an enhancer doesn't need to be located near the transcription initiation site to affect transcription, as some have been found located in several hundred thousand base pairs upstream or downstream of the start site. Enhancers do not act on the promoter region itself, but are bound by activator proteins. These activator proteins interact with the mediator complex, which recruits polymerase II and the general transcription factors, which then begin transcribing the genes. Enhancers can also be found within introns. An enhancer's orientation may even be reversed without affecting its function. Additionally, an enhancer may be excised and inserted elsewhere in the chromosome, and still affect gene transcription. In some alternatives, the enhancers are used to silence the inhibition mechanisms that prevent transcription of the FOXP3 gene. An example of an enhancer binding domain is the TCR alpha enhancer. In some alternatives, the enhancer domain in the alternatives described herein is a TCR alpha enhancer. In some alternatives, the enhancer binding domain is placed upstream from a promoter such that it activates the promoter to increase transcription of the protein. In some alternatives, the enhancer binding domain is placed upstream of a promoter to activate the promoter to increase transcription of the FOXP3 gene.

"Transcriptional activator domains" or "Transcriptional activation domain" as described herein, refers to specific DNA sequences that can be bound by a transcription factor, in which the transcription factor can thereby control the rate of transcription of genetic information from DNA to messenger RNA. Specific transcription factors can include but is not limited to SP1, AP1, C/EBP, heat shock factor, ATF/CREB, c-Myc, Oct-1 and NF-1. In some alternatives, the activator domains are used to silence the inhibition mechanisms that prevent transcription of the FOXP3 gene.

"Ubiquitous chromatin opening element," (UCOE) as described herein, refers to elements that are characterized by unmethylated CpG islands spanning dual, divergently transcribed promoters of housekeeping genes. The UCOE represent promising tools to avoid silencing and sustain transgene expression in a wide variety of cellular models including cell lines, multipotent hematopoietic stem cells, as well as PSCs and their differentiated progeny.

"Operably linked" as used herein refers to functional linkage between a regulatory sequence and a heterologous nucleic acid sequence resulting in expression of the latter.

"Autoimmune disorder" as described herein, refers to abnormally low activity or over activity of the immune system. In cases of immune system over activity, the body attacks and damages its own tissues (autoimmune diseases). Immune deficiency diseases decrease the body's ability to fight invaders, causing vulnerability to infections. Without being limiting, examples of autoimmune disorders or autoimmune diseases can include, for example, systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease, IPEX, Immune dysregulation, polyendocrinopathy, enteropathy, X-linked (IPEX) syndrome and/or Ataxia-telangiectasia. Immune disorders can be analyzed, for example, by examination of the profile of neural-specific autoantibodies or other biomarkers when detected in serum or cerebrospinal fluid in patients. In some alternative methods provided herein, the methods are for treatment, amelioration, or inhibition of autoimmune disorders. In some alternatives, the autoimmune disorder is systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease, IPEX, Immune dysregulation, polyendocrinopathy, enteropathy, X-linked (IPEX) syndrome and/or Ataxia-telangiectasia.

"Organ transplantation" as described herein, is the moving of an organ from one body to another or from a donor site to another location on the person's own body, to replace the recipient's damaged or absent organ. Organs and/or tissues that are transplanted within the same person's body are called autografts. Transplants that are recently performed between two subjects of the same species are called allografts. Allografts can either be from a living or cadaveric source. In some alternatives described herein, a method of treating, inhibiting, or ameliorating side effects of organ transplantation in a subject, such as organ rejection is provided.

Organs that can be transplanted, for example, are the heart, kidneys, liver, lungs, pancreas, intestine, and thymus. Tissues for transplant can include, for example, bones, tendons (both referred to as musculoskeletal grafts), cornea, skin, heart valves, nerves and veins. Kidneys, liver and the heart are the most commonly transplanted organs. Cornea and musculoskeletal grafts are the most commonly transplanted tissues.

In some alternatives described herein, a method of treating, inhibiting, or ameliorating side effects of organ transplantation in a subject, such as organ rejection is provided. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus).

In some alternatives, the subject is selected for inhibition, amelioration, or treatment with the engineered cells of the alternatives herein. In some alternatives, the subject has side effects to anti-inflammatory drugs or anti-rejection drugs. As such, the selected subjects are provided with the alternative cells or compositions provided herein. Side effects from anti-rejection drugs can include interactions with other medications that can raise or lower tacrolimus levels in the blood, kidney toxicity, high blood pressure, neurotoxicity (tremor, headache, tingling, and insomnia), Diabetes mellitus (high blood sugar), diarrhea, nausea, hair loss and/or high potassium. As such, the patients are selected for the methods of treatment, inhibition, or amelioration described herein.

"Organ rejection" or "transplant rejection" as described herein, is when transplanted tissue is rejected by the recipient's immune system, which destroys the transplanted tissue.

"Graft-versus-host disease" (GvHD) as described herein, refers to a medical complication following the receipt of transplanted tissue from a genetically different person. GvHD is commonly associated with stem cell or bone marrow transplant but the term also applies to other forms of tissue graft. Immune cells in the donated tissue recognize the recipient as foreign and not "self." In some alternatives herein, the methods provided can be used for preventing or ameliorating the complications that can arise from GvHD.

"Pharmaceutical excipient" as described herein, is the inert substance that the cells in the composition are provided in.

A "chimeric antigen receptor" (CAR) described herein, also known as chimeric T-cell receptor, refers to an artificial T-cell receptor or a genetically engineered receptor, which grafts a desired specificity onto an immune effector cell. These receptors can be used to graft the specificity of a monoclonal antibody or a binding portion thereof onto a T-cell, for example. In some alternatives herein, the genetically engineered cell further comprises a sequence that encodes a chimeric antigen receptor. In some alternatives, the chimeric antigen receptor is specific for a molecule on a tumor cell. A chimeric antigen receptor or an engineered cell expressing a T cell receptor can be used to target a specific tissue in need for FOXP3. In some alternatives herein comprise methods for targeting specific tissues for providing and delivering FOXP3. In some alternatives, the tissue is a transplanted tissue. In some alternatives, the chimeric antigen receptor is specific for a target molecule on the transplanted tissue.

As described herein, the genetically-engineered cells are engineered to express FOXP3, and as such, they are also described in the alternatives herein as "Treg-phenotype" cells.

DETAILED DESCRIPTION

Many groups are interested in treating auto-immune diseases with regulatory T-cells, due to the possibility for these cells to induce antigen specific tolerance. There are many forms of regulatory T-cells ("$T_{regs}$"), with current nomenclature dividing $T_{regs}$ into those which are generated in the thymus in the course of T-cell development, denoted as thymic regulatory T-cells or "$tT_{regs}$," and peripherally induced regulatory T-cells, denoted as peripheral regulatory T-cells or "$pT_{regs}$."

A key aspect of regulatory T-cell biology is the expression of the transcription factor FOXP3. FOXP3 is thought to be required to specify the regulatory T-cell lineage. This concept is based on the observation that humans who lack FOXP3 develop severe autoimmune disease starting in the neonatal period. One of the most important barriers to the use of either $tT_{regs}$ or $pT_{regs}$ for therapy of autoimmune disease is that FOXP3 expression is subject to epigenetic regulation. In $tT_{regs}$, an upstream region in the FOXP3 gene known as the "thymus specific demethylated region" is completely demethylated, a state, which is thought to result in stable FOXP3 expression. Generally, full demethylation is not observed in $pT_{regs}$. Under inflammatory conditions, FOXP3 may be silenced epigenetically in $pT_{regs}$, and possibly $tT_{regs}$ (although some investigators believe that $tT_{regs}$ are completely stable), potentially resulting in conversion of $pT_{regs}$ to pro-inflammatory CD4 T-cells. The lack of stability of $pT_{regs}$ is a significant concern, as the use of infusion of $pT_{regs}$ that revert to an inflammatory phenotype could result in a worsening of auto-immune symptoms.

Evidence is provided herein that an engineering approach that stabilizes FOXP3 expression in CD4 T-cells allows for the generation of expanded populations of potentially suppressive T-cells that are no longer susceptible to epigenetic modification of their suppressive function. As a result, such cells may have improved properties for therapeutic application.

In the alternatives described herein, the cells for therapeutic application are engineered to have stable FOXP3 expression through the use of a gene editing nuclease to modify the regulatory elements of the FOXP3 locus to provide for stable FOXP3 expression. In the exemplary data provided, a constitutive promoter is placed upstream of the FOXP3 coding exons (examples of constitutive promoters include EF1 alpha promoter, the PGK promoter, and/or the MND promoter, among many others) to drive FOXP3 expression, but a variety of approaches are envisioned to modify the regulatory elements so as to allow for stable FOXP3 expression. By several approaches used to modify the endogenous regulatory elements, the claimed therapeutic cell exhibits constitutive expression of the native FOXP3 gene, such that it is no longer susceptible to regulation that could result in FOXP3 gene silencing and reversion to a non-suppressive cell phenotype. Accordingly, in the alternative methods described herein, the problem of loss of FOXP3 expression due to epigenetic influences on the native regulatory sequences and promoter has been solved.

The proposed method of enforcing FOXP3 expression in a bulk population of CD4 T cells is also an improvement over other approaches to isolating native regulatory T-cell populations as it provides an approach to capture the TCR repertoire present in the inflammatory T-cell population. In patients with auto-immune disease or who are rejecting an organ graft, the endogenous TCR repertoire in the inflammatory T-cell population includes TCR's that have the correct binding specificity to recognize the inflamed tissue or the foreign tissue in the organ. These T-cells are thought to mediate the auto-inflammatory reaction or organ rejection. By converting a portion of the bulk CD4 T-cell population to a regulatory phenotype, the TCR specificities present in the pro-inflammatory population will be represented in the therapeutic cell population. This is an improvement over therapies based on thymic regulatory T-cells, which is thought to have a distinct and non-overlapping TCR repertoire from inflammatory T-cells. In addition, presumably in patients with auto-immune disease or organ rejection, the existing $tT_{reg}$ population has failed to produce the tolerance necessary to avoid inflammation. The methods described herein can be used for therapy of auto-immune disease and for induction of tolerance to transplanted organs.

A significant disadvantage is the need to use gene editing tools that can efficiently carry out the recombination at the FOXP3 locus. As such, the methods provided show that the use of TALEN nuclease can carry this reaction out efficiently, but in principle, any nuclease platform would serve equally well.

The regulatory T cell therapies can be used for tolerance applications in transplantation and in auto-immunity. Currently, Treg infusions are expanded ex vivo. Phase I studies have shown marginal if any efficacy in T1D, and in some cases there have been benefits in post-transplant GvHD. For next generation engineered regulatory T cells, in some alternatives, these can be chimeric antigen receptor (CAR) directed natural $T_{regs}$. Effector T cells can also be converted to $T_{regs}$ by FOXP3 expression.

However there may also be differences between engineered versus natural $T_{regs}$ for methods of treatment. Natural Treg therapy has been considered safe, however too few natural $T_{regs}$ causes autoimmunity. Treg play a critical role in multiple autoimmune diseases (IPEX, T1D, SLE, RA, EAE, etc). Approaches to augment human Treg number or function are in current trials including low-dose IL-2 and adoptive transfer of autologous expanded Treg. The efficacy of IL-2 therapy is limited due to its pleotropic activity and potential "off target" effects that may increase inflammation. Adoptive Treg therapy is likely limited by in vivo stability and viability of expanded $T_{regs}$ and their lack of relevant antigen specificity.

There are also potential flaws with the use of natural $T_{regs}$. For example, autoimmune patients are genetically predisposed to Treg instability. For example, it is plausible for a CAR bearing nTreg to convert to a CAR T effector cell. nTreg also retain the potential for epigenetic regulation of FOXP3, which could lead to the down regulation of FOXP3 induction, which means that the function or an nTreg population may never be fully predictable. Also, natural $T_{regs}$ may not include the correct TCR (T cell receptor) specificities. The Treg function may also be linked to a selectable marker in which the expanded native Treg cell population may always have contaminating inflammatory cells. Thus the methods provided herein are an improvement over using the transfer of natural $T_{regs}$ by using engineered cells as there is potential for linking CAR expression to regulatory T cell function to avoid potential engraftment of CAR $T_{regs}$ that have the potential to convert to pro inflammatory CAR T cells.

Figure 2:
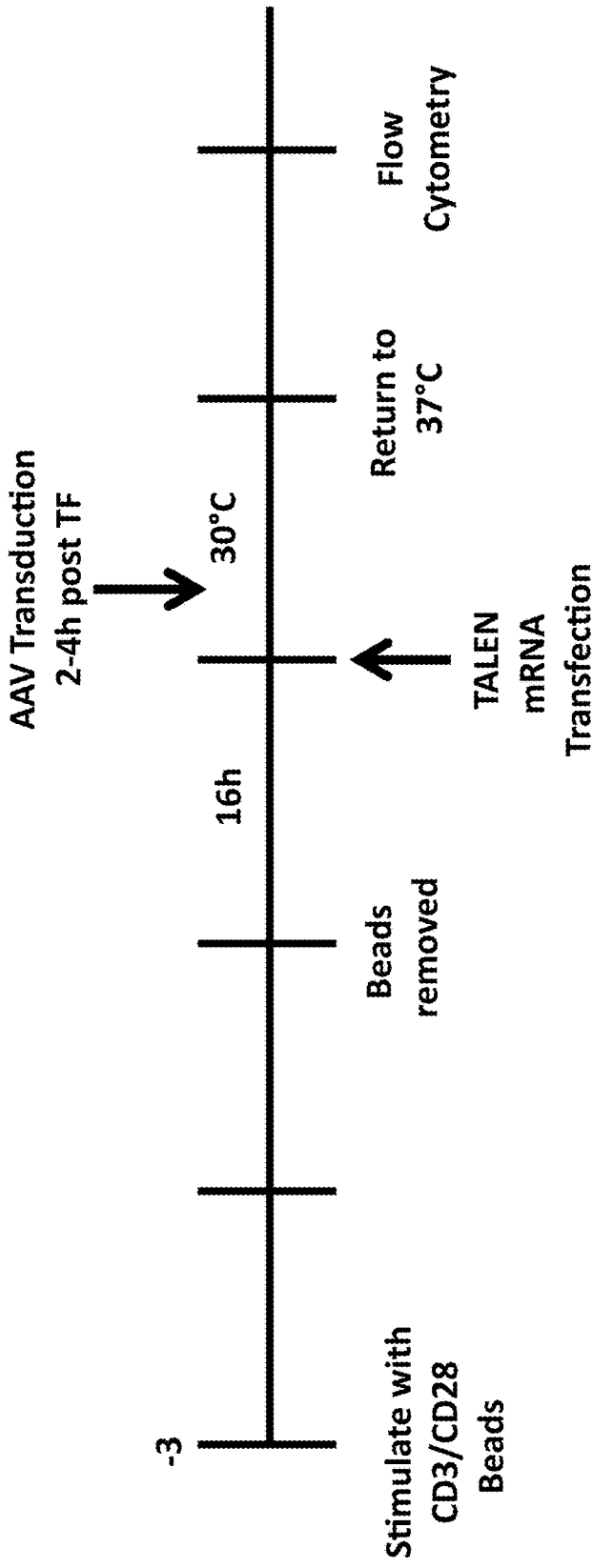
FIG. 2: Tools for T cell editing. As shown in the Figure efficient methods for nuclease and repair template—codelivery is in place for the alternative methods provided herein. As shown, T cells are activated and expanded. The T cells are stimulated with CD3/CD28 beads which are then removed. TALEN delivery is then performed via mRNA electroporation. The editing template is delivery by an adeno-associated virus.

The tools for T-cell editing for engineering a T cell for protein expression are well known (See for example FIG. 2). For example, T-cells activated and expanded, TALEN delivery is performed via mRNA electroporation, the template can be edited by a delivered Adeno-Associated Virus (high MOI transient expression—recombinant AAV is non-integrating).

Figure 3:
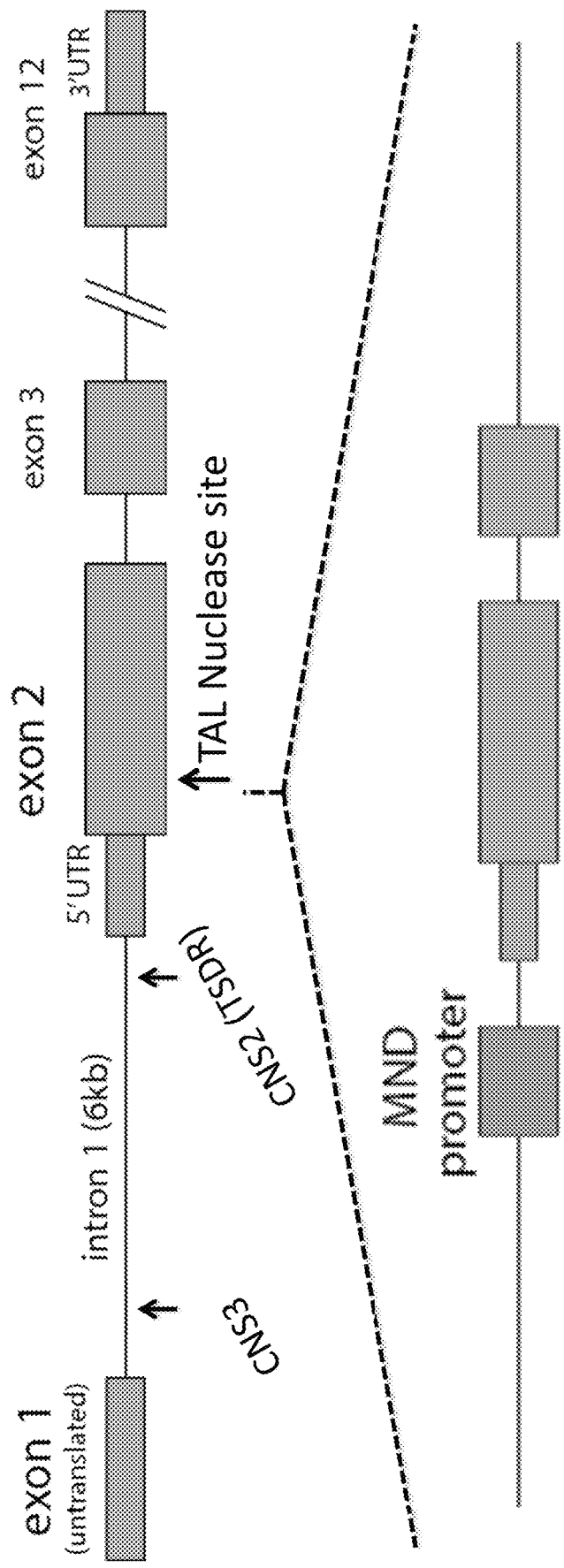
FIG. 3: Enforcing FOXP3 expression through gene-editing. As described in the alternatives herein, FOXP3 expression through gene-editing can be used to bypass the epigenetic regulation. Design of a stable, site specific integration of a promoter upstream of the FOXP3 coding region could override traditional control. Foxp3 expression is traditionally controlled through epigenetic regulation of the intronic region (intron 1) upstream of the first coding exon (exon 2). In resting Naïve T cells, the FOXP3 locus is epigenetically 'closed' (FOXP3−). Thymically derived, natural Tregs have an 'open' locus (FOXP3+) Induced Tregs (iTregs) have a partially open locus (FOXP3+-unstable).

FOXP3 can then be expressed through gene editing processes in which a promoter is inserted upstream from the first coding exon and downstream from natural regulatory elements which are controlled by epigenetic control mechanisms. Control of expression by insertion of the promoter upstream from the first promoter has not yet been reported and led to the surprising result of a constitutive upregulation of FOXP3 that cannot be downregulated by epigenetic control. Shown in FIG. 3, is the insertion of a promoter, such as an MND promoter into the FOXP3 gene. As shown, Foxp3 expression is traditionally controlled through epigenetic regulation of the Intronic region (intron 1) upstream of the first coding exon.

Figure 4:
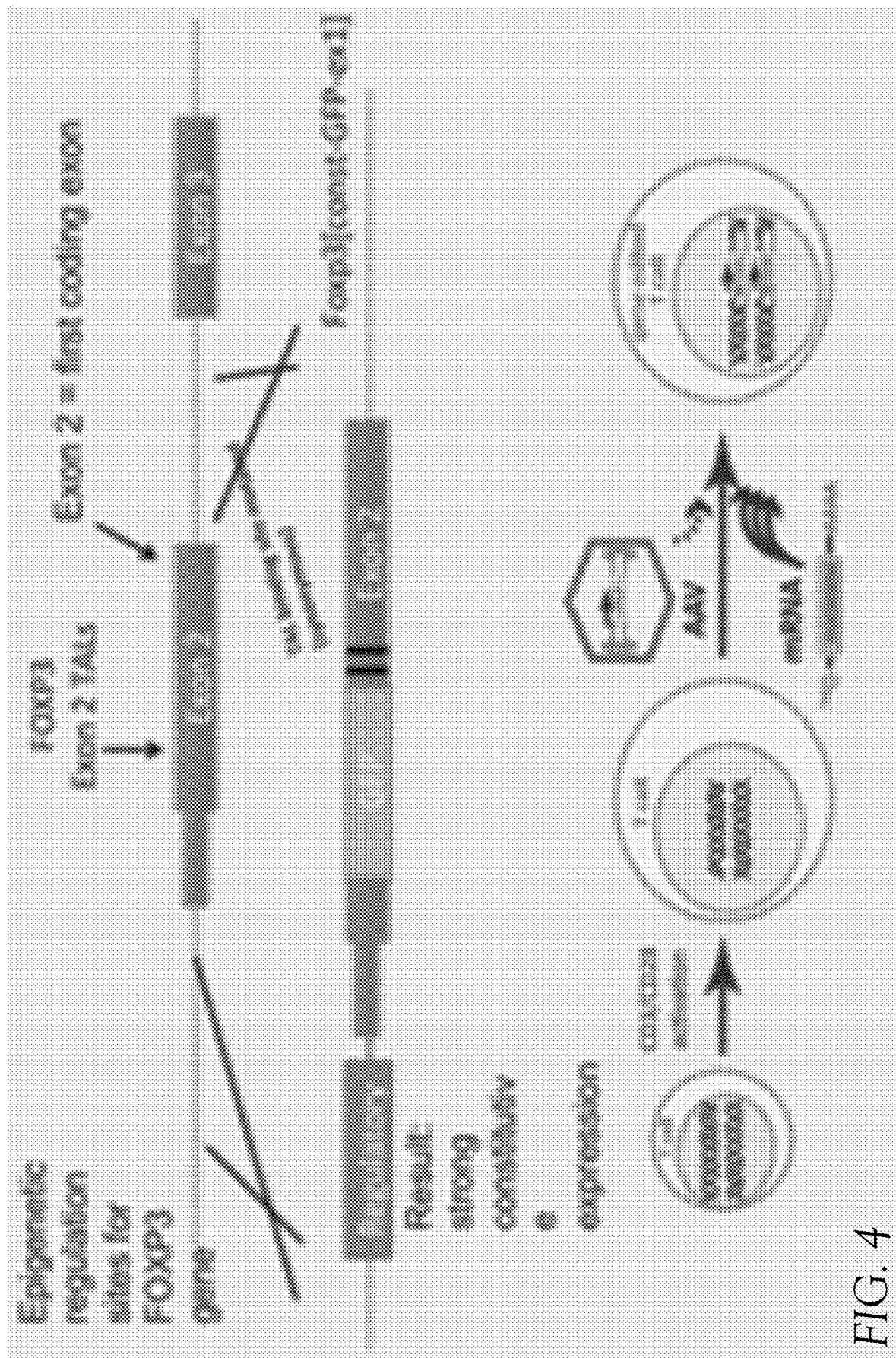
FIG. 4: HDR targeting to engineer FOXP3+ stabilized cells. As shown in the figure epigenetic regulation sites for the FOXP3 gene resides upstream from FOXP3 gene. In order to engineer a FOXP3+ stabilized T cell, T-cells are provided and first activated with CD3/CD28. The editing template is delivery by an adeno-associated virus, and an mRNA coding for a nuclease is introduced into the T cell to engineer a gene edited T cell.
Figure 5:
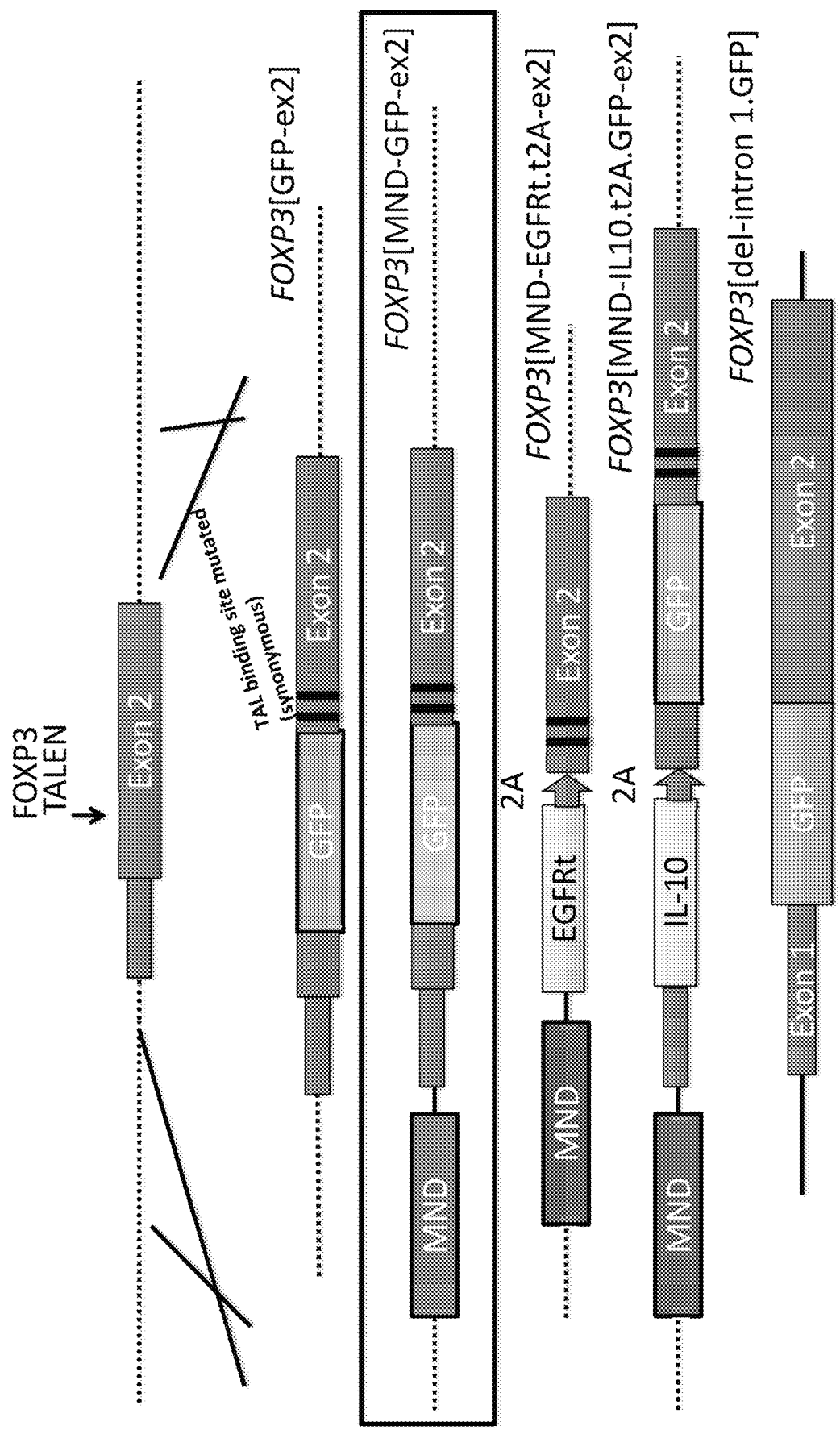
FIG. 5: Gene Editing Template design is highly flexible. As shown in the Figure, five constructs were constructed: GOXP3 [GFP-ex2], FOXP3 [MND-GFP-ex2], FOXP3 [MND-EGFRt.t2A-ex2], FOXP3 [MND-IL10.t2A.GFP-ex2] and FOXP3 [del-intron1.GFP].

As shown in FIG. 4, HDR targeting is used to engineer FOXP3+ stabilized T cells, which results in strong constitutive expression. Shown in FIG. 5, are templates of the gene constructs that were used in the alternatives described herein.

Methods of controlling expression of FOXP3 are also provided. In some alternatives, the promoter inserted upstream from the FOXP3 coding exon is an inducible receptor. In some alternatives, the system employs a synthetic transcriptional regulator, which, in the presence of tamoxifen, binds a synthetic promoter upstream of a transgene to induce expression of FOXP3. In the presence of tamoxifen, binding of TamR-tf to 7×HBD/EF1αp promoter induces the "ON" state of transgene expression. In some alternatives, this transcriptional regulator is modified to provide for a varying level of control of transgene expression.

In some alternatives, the cells can also be further engineered to express a chimeric antigen receptor or a TCR (T cell receptor) or other targeting moiety. The cells can be engineered to express a CAR for targeting a specific tissue or cell. In some alternatives, the CAR comprises a ligand binding domain, which is a tumor specific molecule, viral molecule, or another molecule expressed on a target cell population. In some alternatives, the targeted tissue has low expression of FOXP3. Allowing a T-cell to express a CAR or TRC would allow the T-cell to target a specific tissue in need for the delivery of cells expressing FOXP3 to a tissue specific site.

Figure 6:
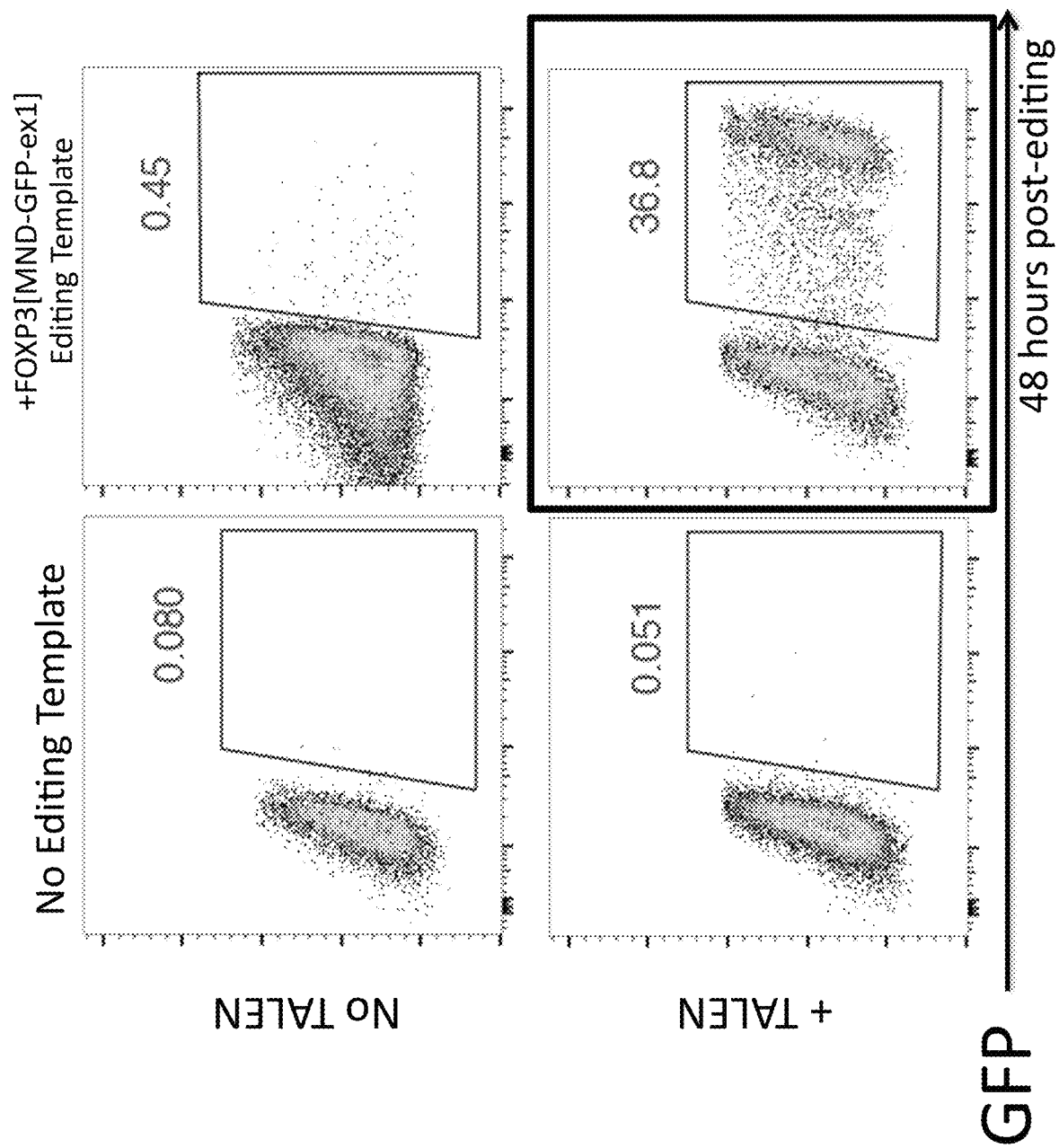
FIG. 6 shows that Gene editing efficiently targets the FOXP3 gene and drives high expression of transgene. As shown in the Figure cells that were engineered to express GFP fused to the N-terminus of the endogenous FOXP3 gene under the control of an MND promoter showed high level GFP-FOXP3 fusion protein expression in comparison to the cells that did not have the TALEN nuclease introduced into the T-cell.
Figure 7:
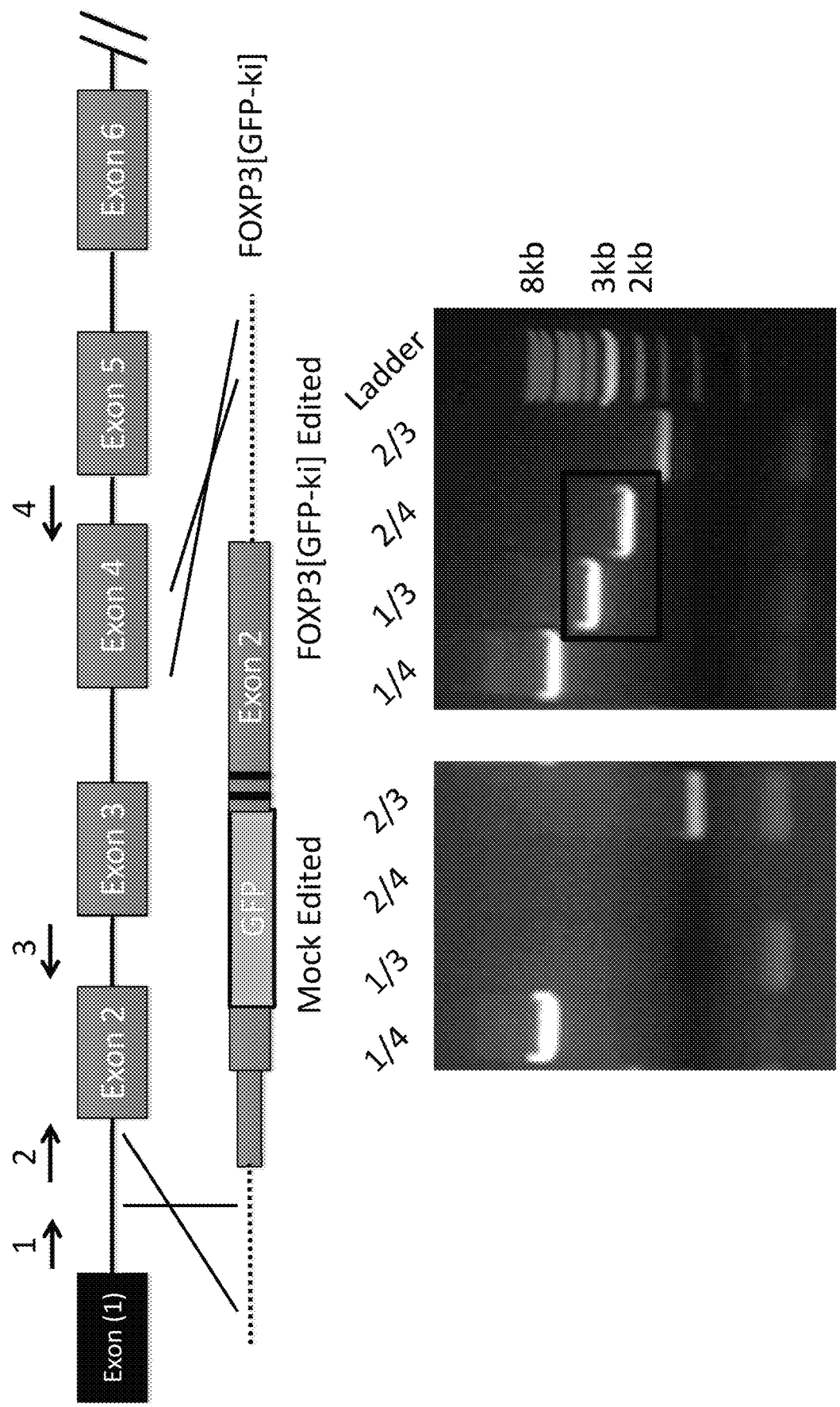
FIG. 7: Edited cells show seamless HR mediated integration at targeting site. PCR was performed with the indicated primer sets (i.e. corresponding to the positions of the red arrow on the figure), and the resulting PCR products were analyzed by agarose gel electrophoresis. PCR using one primer outside of the targeting template (Primer 1 or Primer 2) and one inside (either primer 3 or primer 4) will only show a band of the correct size if precise targeted integration occurs. The gel fragment on the left demonstrates the lack of targeted integration in mock edited cells, while that on the right shows the presence of correct sized bands in the edited cells.

Alternative 1: Gene Editing Efficiently Targets the FOXP3 Gene and Drives High Expression of the Transgene As shown in the FIG. 6, cells that were engineered to express GFP fused to the N-terminus of the endogenous FOXP3 gene under the control of an MND promoter showed high level GFP-FOXP3 fusion protein expression in comparison to the cells that did not have the TALEN nuclease introduced into the T-cell. As shown in FIG. 7, edited cells show seamless HR mediated integration at targeting site. For the experiment in FIG. 7, PCR was performed with the indicated primer sets (i.e. corresponding to the positions of the red arrow on the figure), and the resulting PCR products were analyzed by agarose gel electrophoresis. PCR using one primer outside of the targeting template (Primer 1 or Primer 2) and one inside (either primer 3 or primer 4) will only show a band of the correct size if precise targeted integration occurs. The gel fragment on the left demonstrates the lack of targeted integration in mock edited cells, while that on the right shows the presence of correct sized bands in the edited cells.

Figure 8:
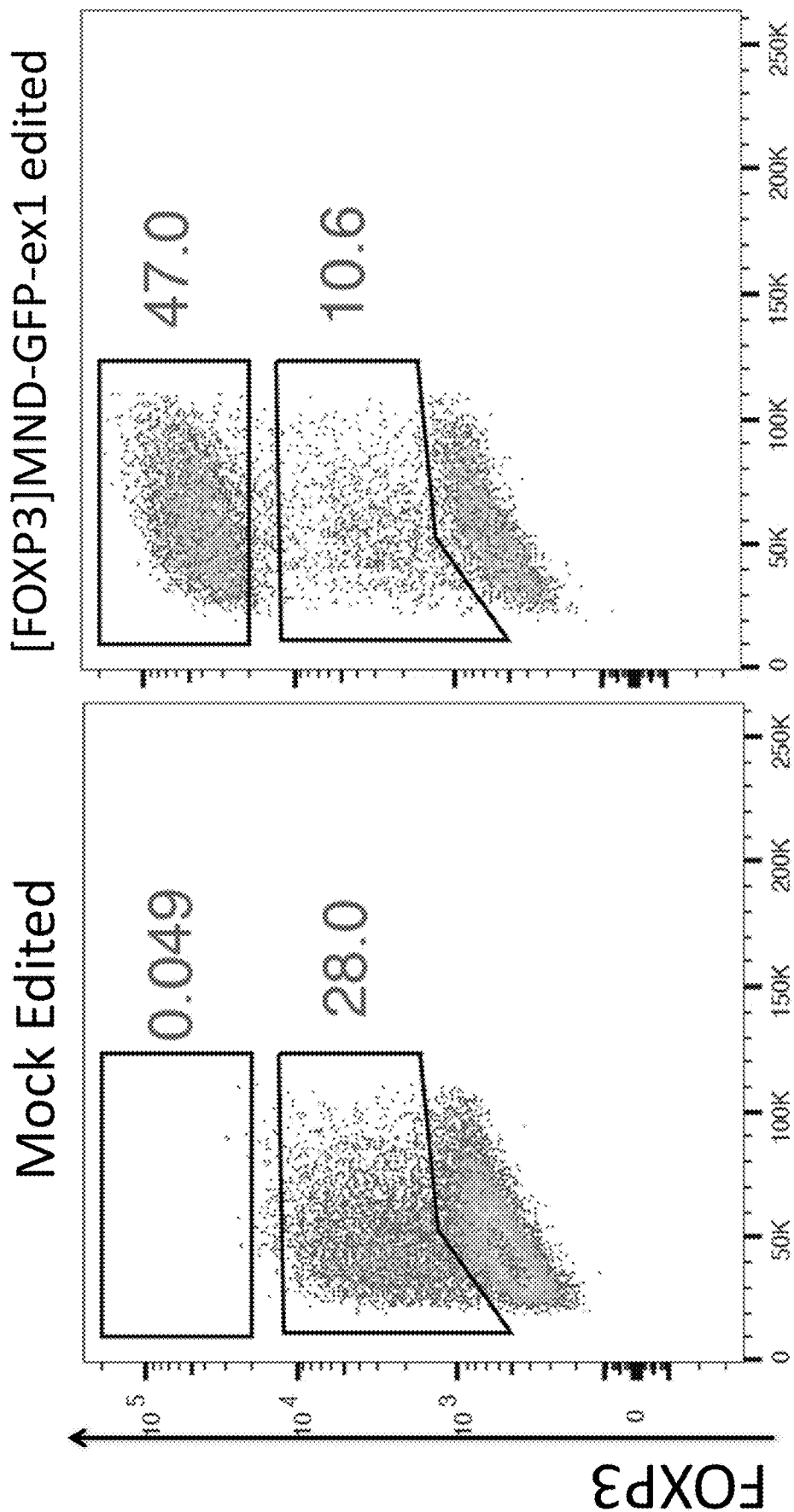
FIG. 8: GFP/FOXP3 fusion results in consistent, high-level Foxp3 expression. As shown in the Figure, the GFP FOXP3 fusion led to induction of FOXP3 expression under the control of an MND promoter over the mock-edited cells. Shown are flow cytometry analyses of FOXP3 expression in mock edited vs. edited cells, with FOXP3 expression is shown on the Y-axis, and forward scatter is shown on the x-axis.

The GFP/FOXP3 fusion results in consistent, high-level Foxp3 expression. As shown in the Figure, the GFP FOXP3 fusion led to induction of FOXP3 expression under the control of an MND promoter over the mock-edited cells. Shown are flow cytometry analyses of FOXP3 expression in mock edited vs. edited cells, with FOXP3 expression is shown on the Y-axis, and forward scatter is shown on the x-axis (FIG. 8).

Figure 9:
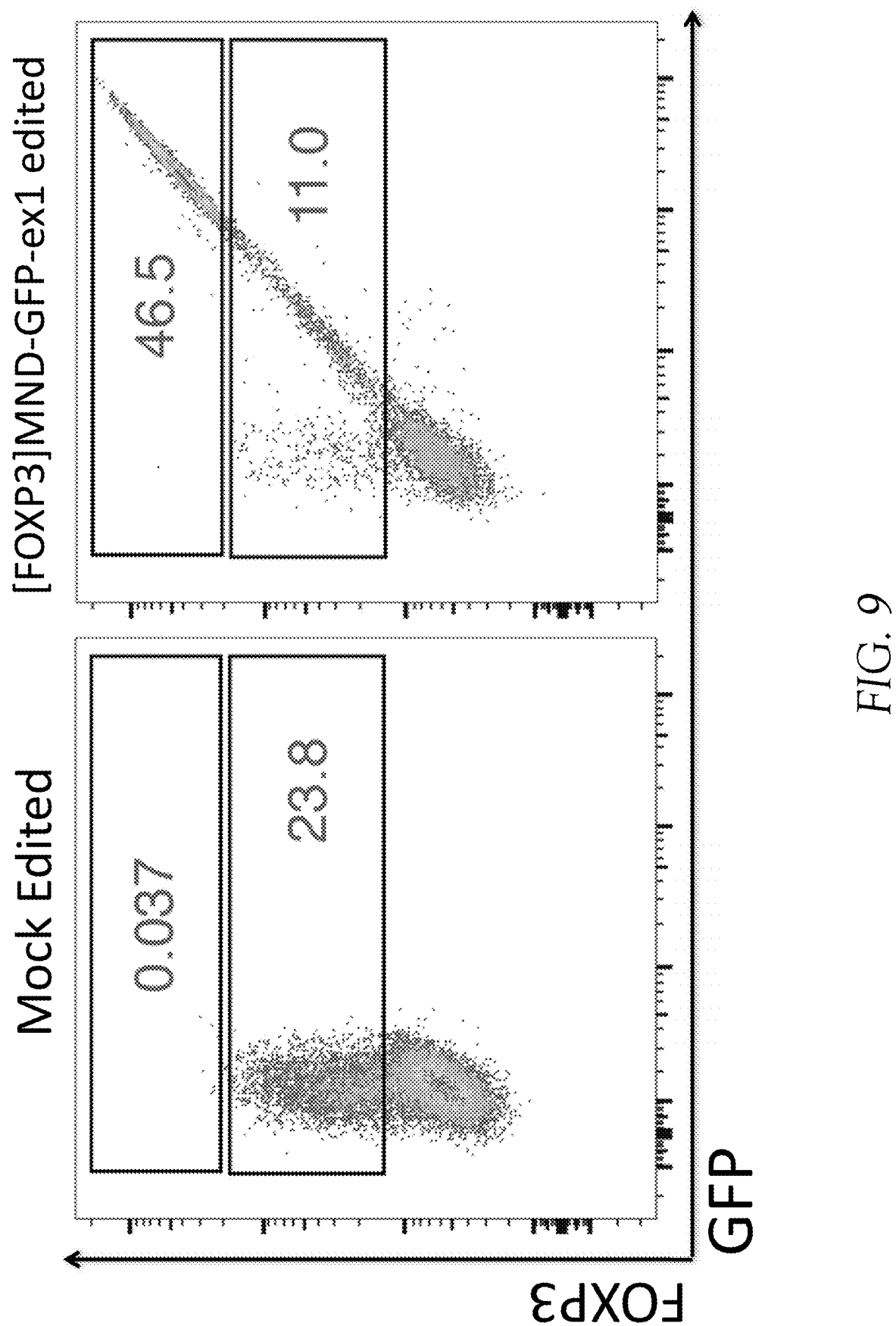
FIG. 9: GFP/FOXP3 fusion results in consistent, high-level Foxp3 expression. As shown in the Figure, the GFP FOXP3 fusion led to induction of FOXP3 expression under the control of an MND promoter over the mock-edited cells. Shown are flow cytometry analyses of FOXP3 expression and GFP expression in mock edited vs. edited cells, with FOXP3 expression shown on the Y-axis, and GFP shown on the x-axis of each plot.

GFP/FOXP3 fusion results in consistent, high-level Foxp3 expression. As shown in FIG. 9, the GFP FOXP3 fusion led to induction of FOXP3 expression under the control of an MND promoter over the mock-edited cells. Shown are flow cytometry analyses of FOXP3 expression and GFP expression in mock edited vs. edited cells, with FOXP3 expression shown on the Y-axis, and GFP shown on the x-axis of each plot. (See FIG. 9).

As shown in the experiments of these exemplary alternatives, gene editing efficiently targets the FOXP3 gene and drives high expression of the transgene.

As the experiments provided herein are done in vitro, it is hard to predict that the same high-levels of FOXP3 expression can be maintained in in vivo tests, cells or subjects. As such cells used for treatment will need to be monitored in the subject to see if the cells are maintained, increased or decreased. Methods to examine subjects for engineered cells after administration are known to those skilled in the art. For example, commercially available technology through Adaptive Biotech Technology have a system to immune sequence B and T cells to detect a specific cell, such as an engineered cell to determine if the cell is maintained, increased or decreased. As the cells may have been edited at different distances upstream from a coding exon, this may affect the expression of FOXP3 in in vivo, as such in vivo data does not predict the outcome in in vivo experiments. Furthermore, the use of different promotors, effector domains and activation domains may have a different outcome.

Figure 10:
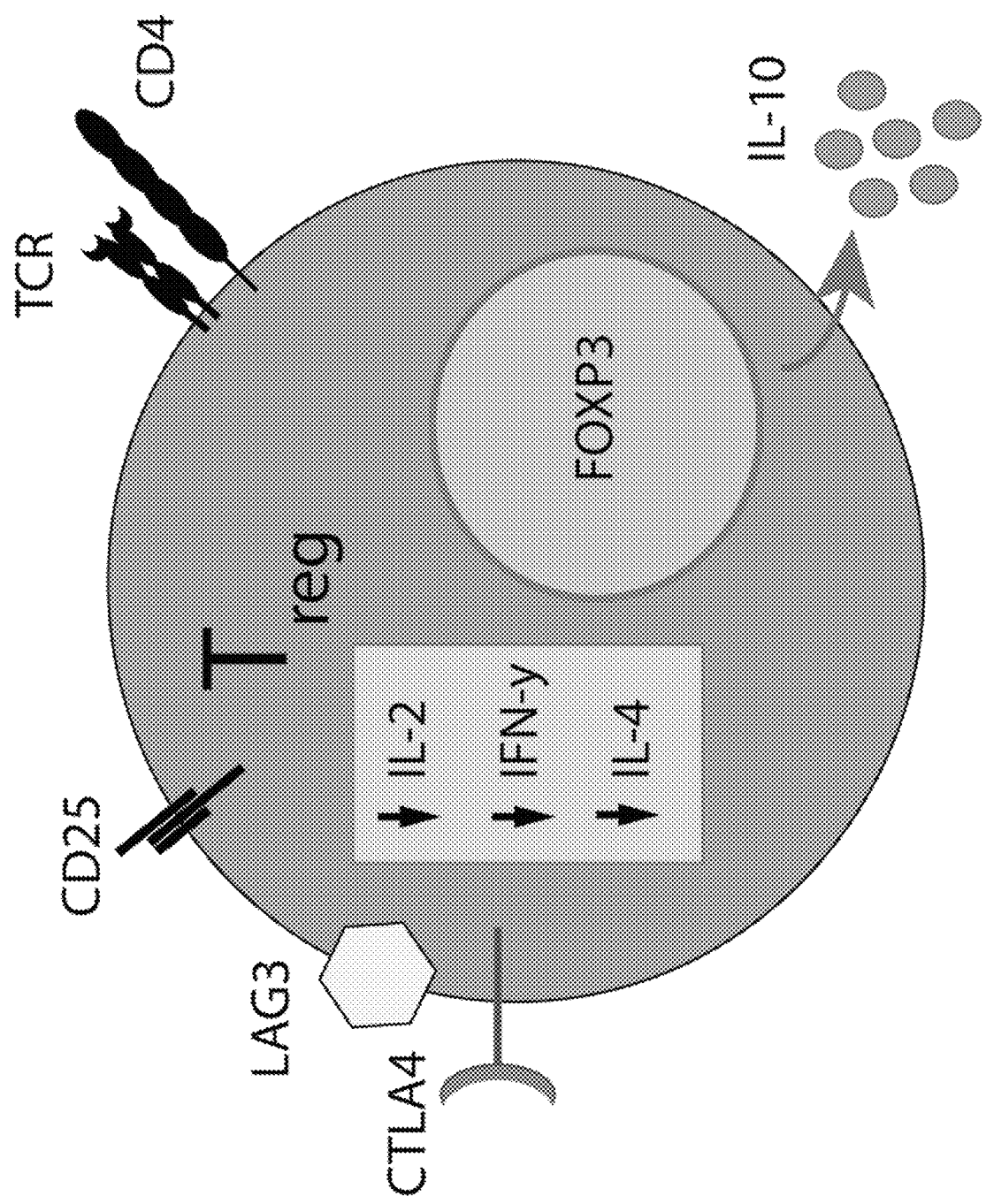
FIG. 10: Cartoon of Treg cell illustrating surface marker and cytokine phenotype.
Figure 11:
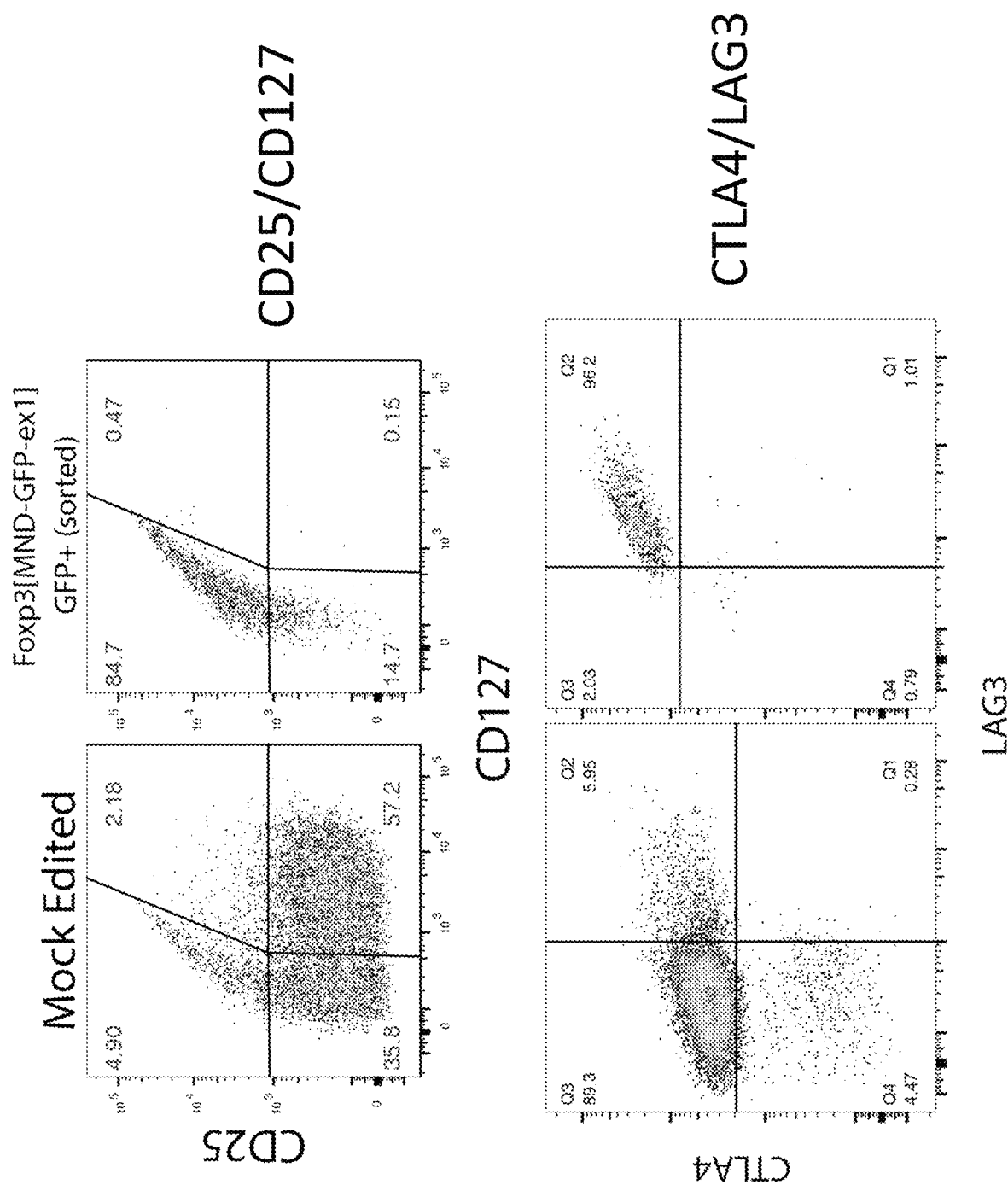
FIG. 11: Edited Cell Surface Phenotype. As shown in the Figure, engineered T cells that stably expressed FOXP3 were analyzed by flow cytometry for expression of CD25, CD127, CTLA4 and LAG3. Analogous to natural regulatory T-cells, the engineered cells express high CD25, low CD127, and high CTLA4 and Lag3.

Alternative 2: Enforced Expression of FOXP3 Results in T Cells with a $T_{reg}$ Surface and Cytokine Phenotype FIG. 10 shows a cartoon of T-reg cell illustrating surface marker and cytokine phenotype. It was desired to see if edited cells have a specific surface phenotype. As shown in FIG. 11, engineered T cells that stably expressed FOXP3 were analyzed by flow cytometry for expression of CD25, CD127, CTLA4 and LAG3. Analogous to natural regulatory T-cells, the engineered cells were shown to express high CD25, low CD127, and high CTLA4 and Lag3.

Figure 12:
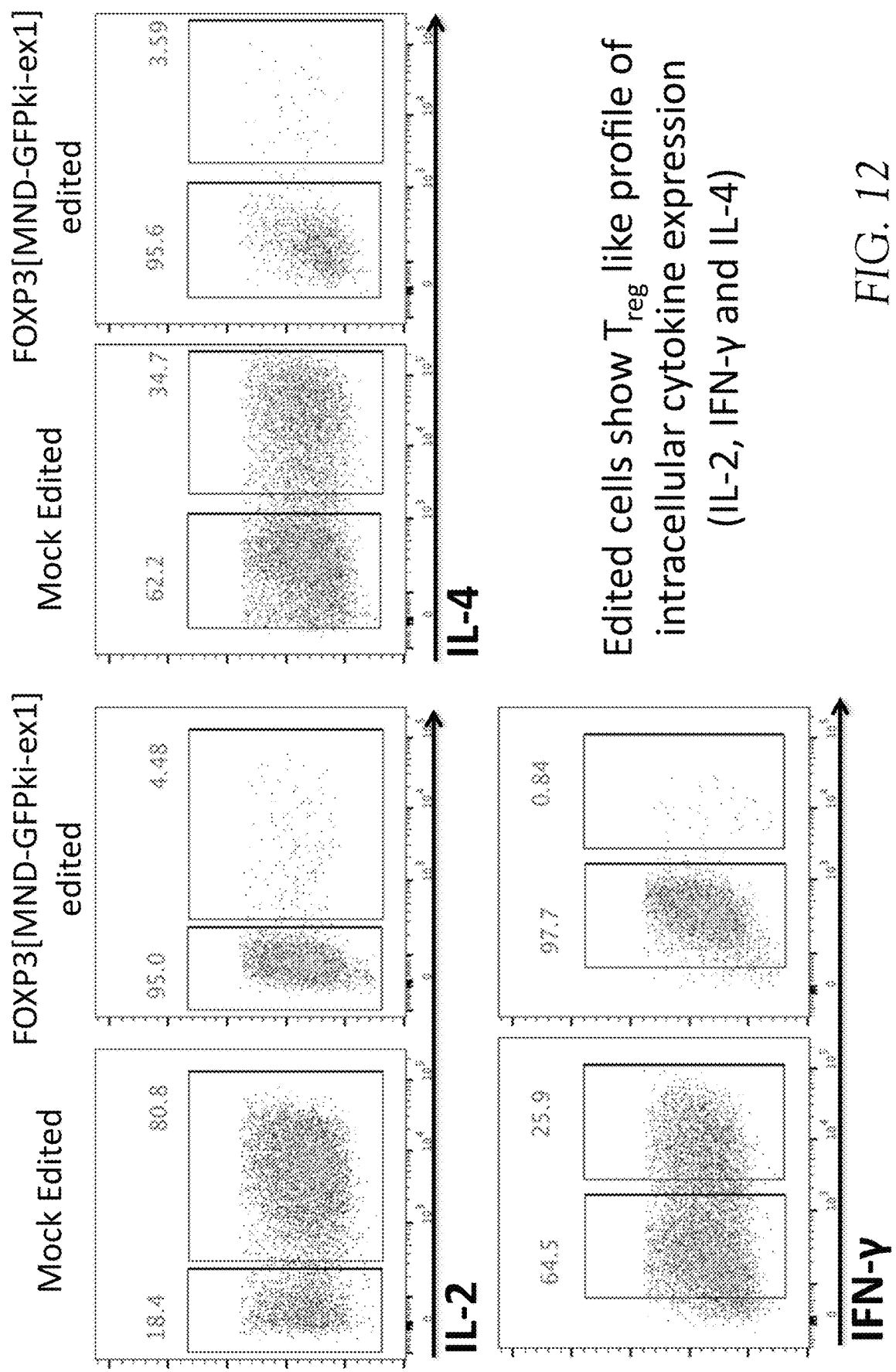
FIG. 12: Cytokine Expression Profile of Edited Cells. As shown in the Figure, the engineered cells show a $T_{reg}$ like profile of intracellular cytokine expression as compared to the mock edited T cells, with low expression of IL2, IL4, and IFN-g.
Figure 13:
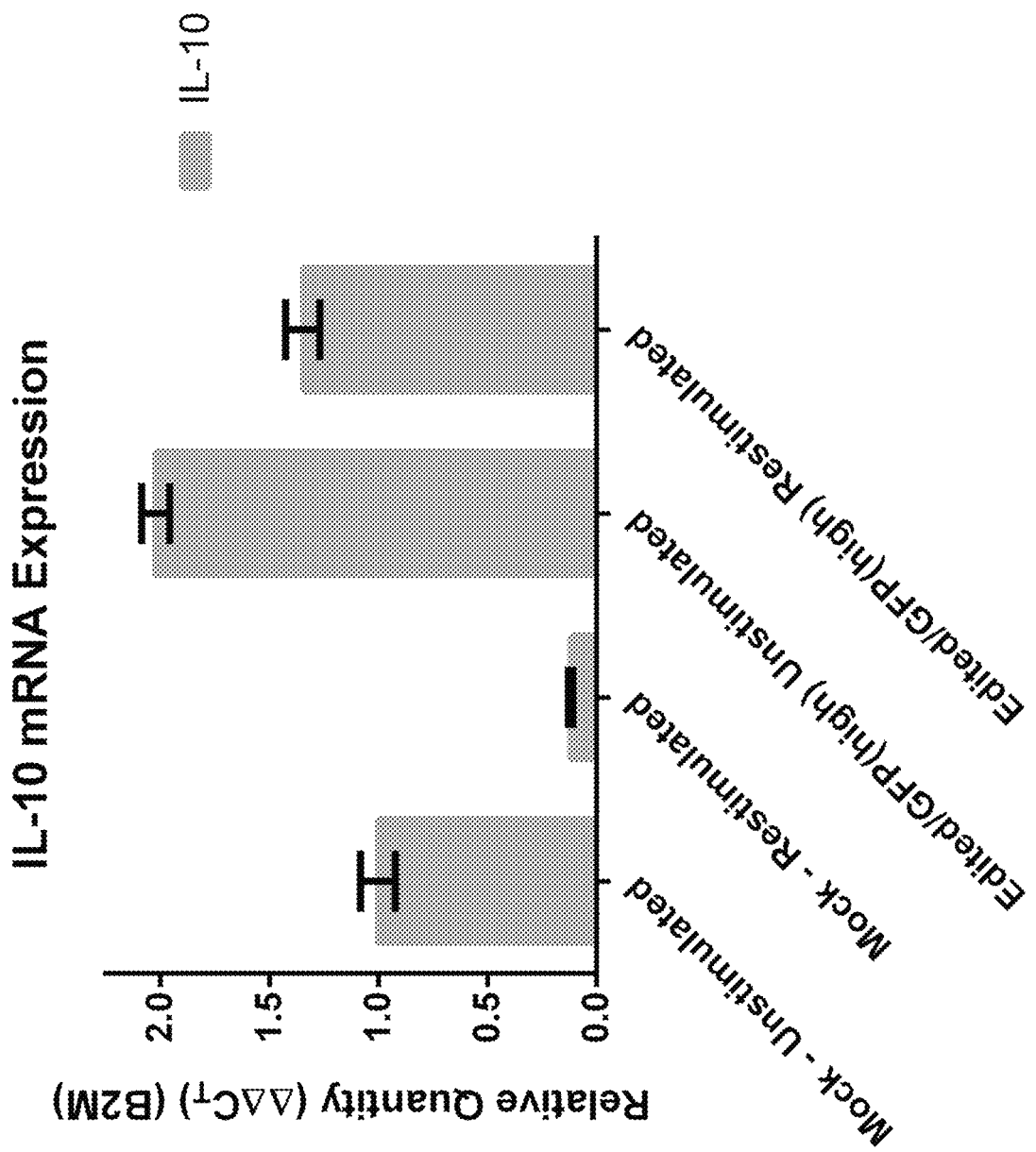
FIG. 13: Cytokine Expression Profile of Edited Cells. As shown in the bar graph, the engineered T cells stably expressing FOXP3 showed a high expression of IL-10 relative to mock edited cells.
Figure 14:
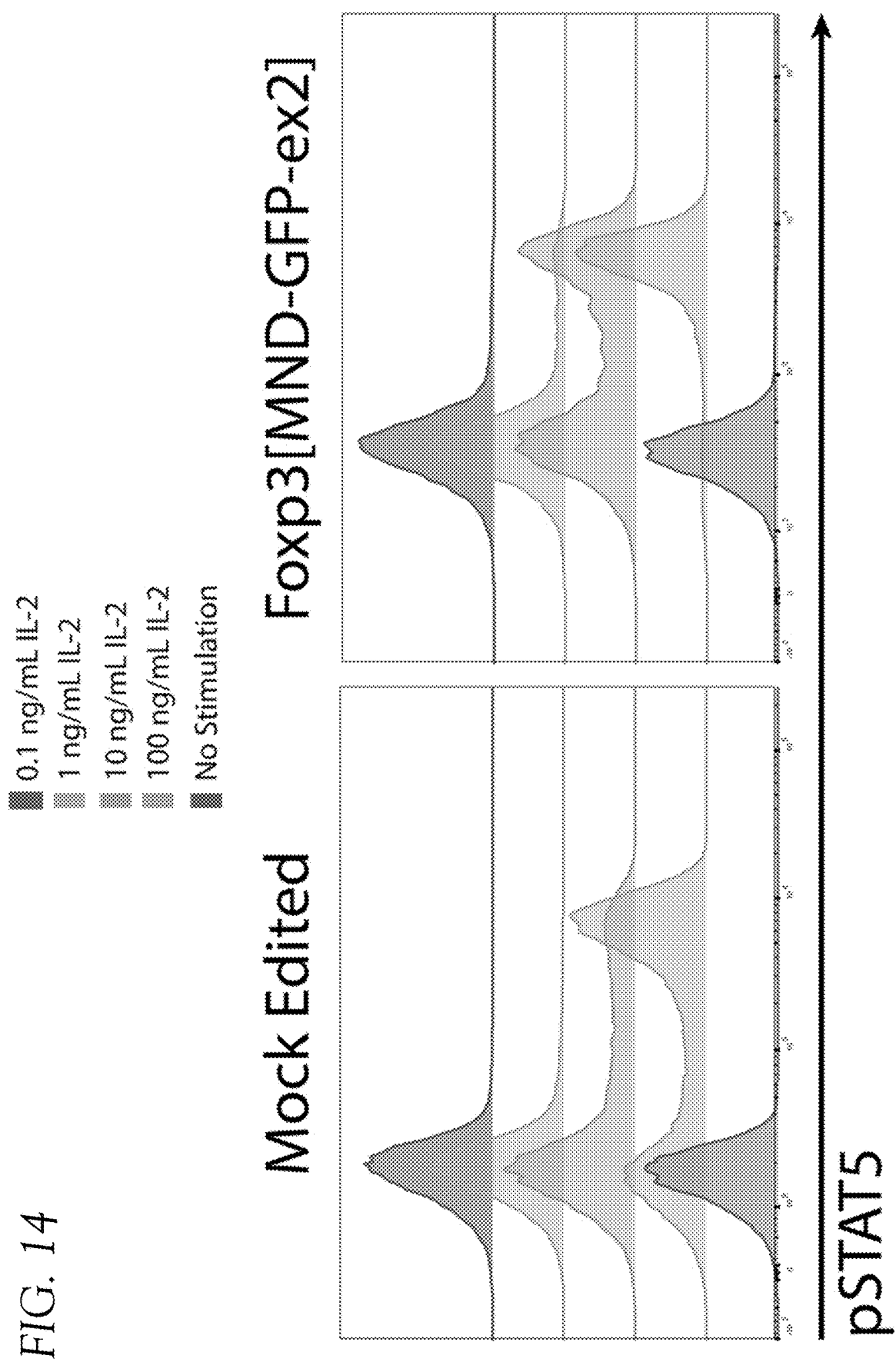
FIG. 14: IL2/STAT5 Signaling Sensitivity. Natural Tregs are highly sensitive to IL2 due to their high expression of CD25. Mock edited and edited cells were compared for their sensitivity to IL2 signaling by exposure to different concentrations of IL2 in vitro. Response to IL2 was measured by extent of phosphorylation of STAT5. As can be seen, the edited cells who stat5 phosphorylation indicative of IL2 signaling at much lower concentrations of IL2 relative to mock edited cells. The profiles from top to bottom are: 0.1 ng/ml IL/2, 1 ng/ml IL/2, 10 ng/ml IL/2, 100 ng/ml IL/2, and no stimulation.

The cytokine expression profile of edited cells is also shown in FIG. 12. As shown in FIG. 12, the engineered cells show a $T_{reg}$ like profile of intracellular cytokine expression as compared to the mock edited T cells, with low expression of IL2, IL4, and IFN-g. As shown in the bar graph of FIG. 13, the engineered T cells stably expressing FOXP3 showed a high expression of IL-10 relative to mock edited cells It was also shown that the edited cells have IL2/STAT5 signaling sensitivity (FIG. 14). Natural Tregs are highly sensitive to IL2 due to their high expression of CD25. Mock edited and edited cells were compared for their sensitivity to IL2 signaling by exposure to different concentrations of IL2 in vitro. Response to IL2 was measured by extent of phosphorylation of STAT5. As can be seen, the edited cells who stat5 phosphorylation indicative of IL2 signaling at much lower concentrations of IL2 relative to mock edited cells.

Figure 15:
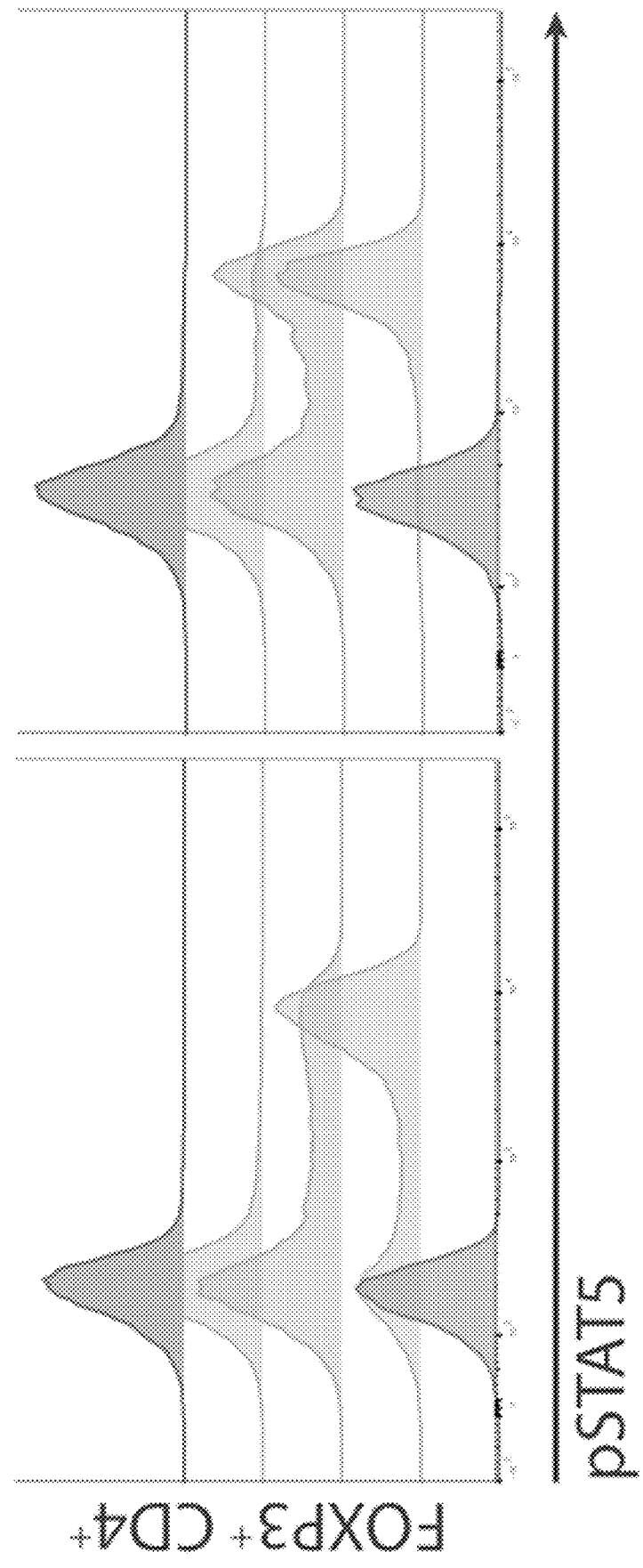
FIG. 15: IL2/STAT5 Signaling Sensitivity (FOXP3+ subset). Natural Tregs are highly sensitive to IL2 due to their high expression of CD25. Mock edited and edited cells were compared for their sensitivity to IL2 signaling by exposure to different concentrations of IL2 in vitro. Response to IL2 was measured by extent of phosphorylation of STAT5. As can be seen, the edited cells who stat5 phosphorylation indicative of IL2 signaling at much lower concentrations of IL2 relative to mock edited cells. The profiles from top to bottom are: 0.1 ng/ml IL/2, 1 ng/ml IL/2, 10 ng/ml IL/2, 100 ng/ml IL/2, and no stimulation.

As shown in FIG. 15, natural $T_{regs}$ are highly sensitive to IL2 due to their high expression of CD25. Mock edited and edited cells were compared for their sensitivity to IL2 signaling by exposure to different concentrations of IL2 in vitro. Response to IL2 was measured by extent of phosphorylation of STAT5. As can be seen, the edited cells who stat5 phosphorylation indicative of IL2 signaling at much lower concentrations of IL2 relative to mock edited cells.

As shown in this exemplary alternative, the enforced expression of FOXP3 results in T cells with a $T_{reg}$ surface and cytokine phenotype.

As some of the experiments provided herein are done in vitro, it is hard to predict that the same elevated levels of FOXP3 expression in cells can be maintained in in vivo tests, cells or subjects and that such elevated levels of FOXP3 expression in cells will be sufficient to ameliorate a pathogenic T-cell and/or B-cell response in an autoimmune disorder or GVHD, for example. It is also difficult to predict that the cells will have T regulatory cell characteristics in vivo. As such it may be advantageous for cells used for treatment, inhibition, or amelioration to be monitored in a subject to determine if the cells are maintained, increased or decreased before, during and/or after treatment. Methods to examine subjects for engineered cells after administration are known to those skilled in the art. For example, commercially available technology through Adaptive Biotechnologies and others is a system to sequence B and T cells to detect specific types of immune cells, such as an engineered cell or pathogenic B- or T-cell to determine if the cell is maintained, increased or decreased. As the cells may have been edited at different distances upstream from a coding exon, this may affect the expression of FOXP3 in vivo, as such the in vivo data does not predict the outcome in in vivo experiments. Furthermore, the use of different promotors, effector domains and activation domains may have a different outcome.

In some alternatives, of the methods of treatments described herein, the methods further comprises monitoring the subject to determine if the engineered cells are maintained, increased or decreased before, during and/or after treatment. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject.

The cells in vivo would also have to be tested to see if they also express similar marker to T regulatory cells.

Figure 16:
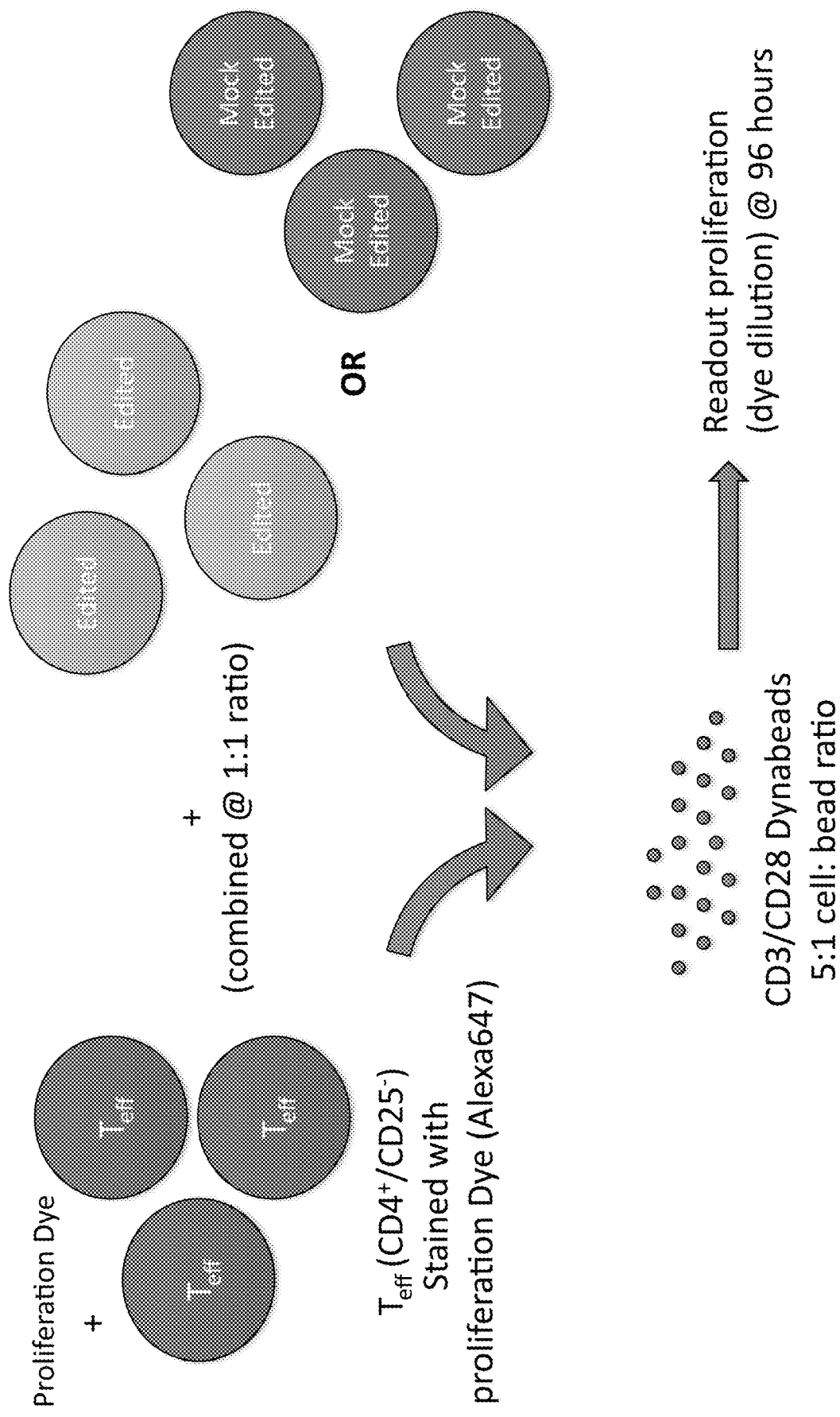
FIG. 16: Schematic of an assay to read out suppressive activity of regulatory T-cells. CFSE labeled responder cells are mixed with edited Tregs or mock edited cells, and bead stimulated. Assay is read out by extent of CFSE dilution at 96 hours.

Alternative 3: Edited Cell Functional Activity, Edited Cells Can Suppress Teff Proliferation Shown in FIG. 16 is a schematic of an assay to read out suppressive activity of regulatory T-cells. CFSE labeled responder cells are mixed with edited Tregs or mock edited cells, and bead stimulated. The assay is read out by extent of CFSE dilution at 96 hours.

Figure 17:
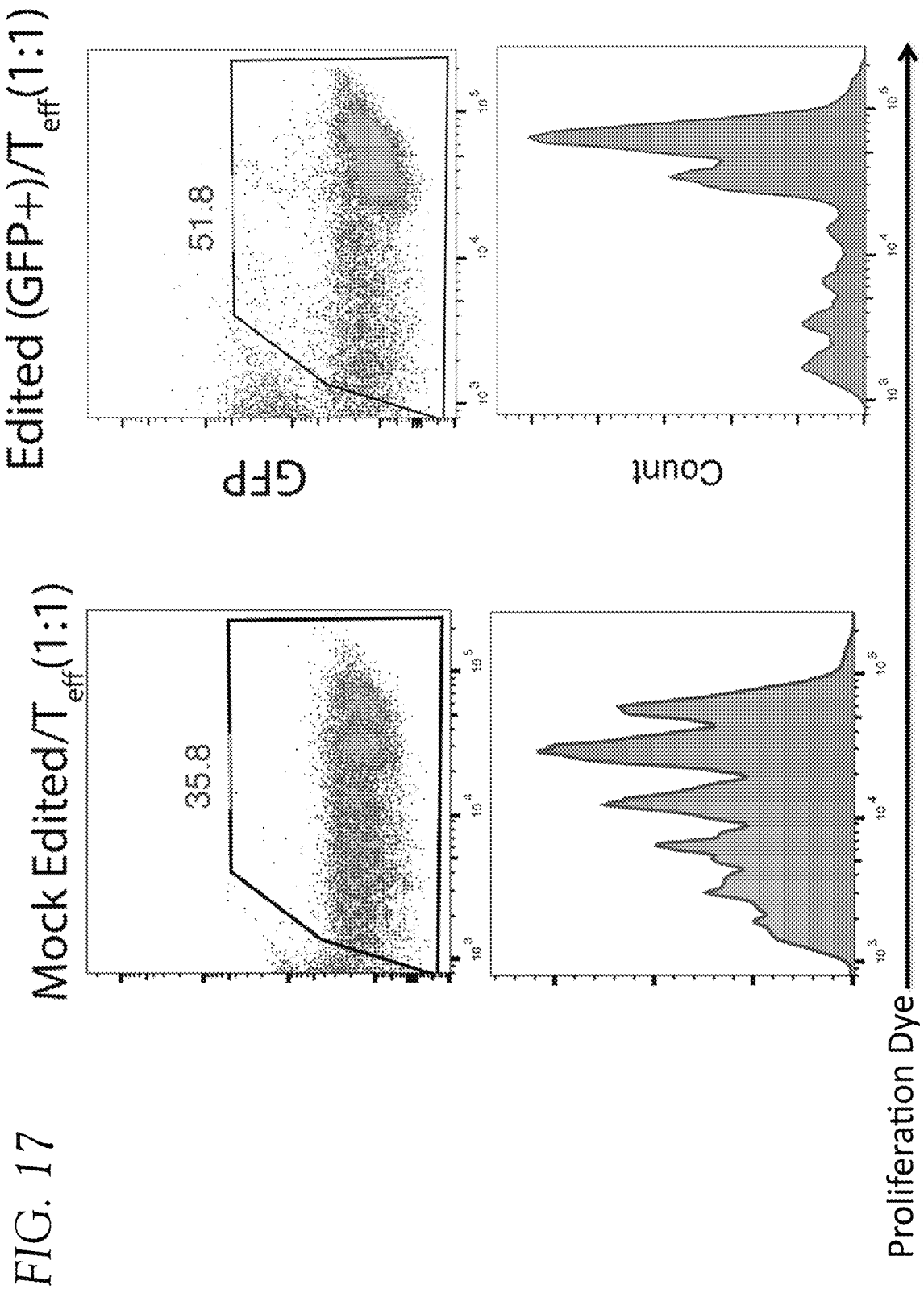
FIG. 17: Edited T Cells can suppress $T_{eff}$ proliferation. Responder cells incubated with mock edited cells are able to substantially dilute the CFSE label through their proliferation, whereas responder cells incubated with engineered GFP+ cells mostly remain undivided (with high amounts of remaining label).

FIG. 17 shows that the edited T Cells can suppress $T_{eff}$ proliferation. Responder cells incubated with mock edited cells are able to substantially dilute the CFSE label through their proliferation, whereas responder cells incubated with engineered GFP+ cells mostly remain undivided (with high amounts of remaining label).

Figure 18:
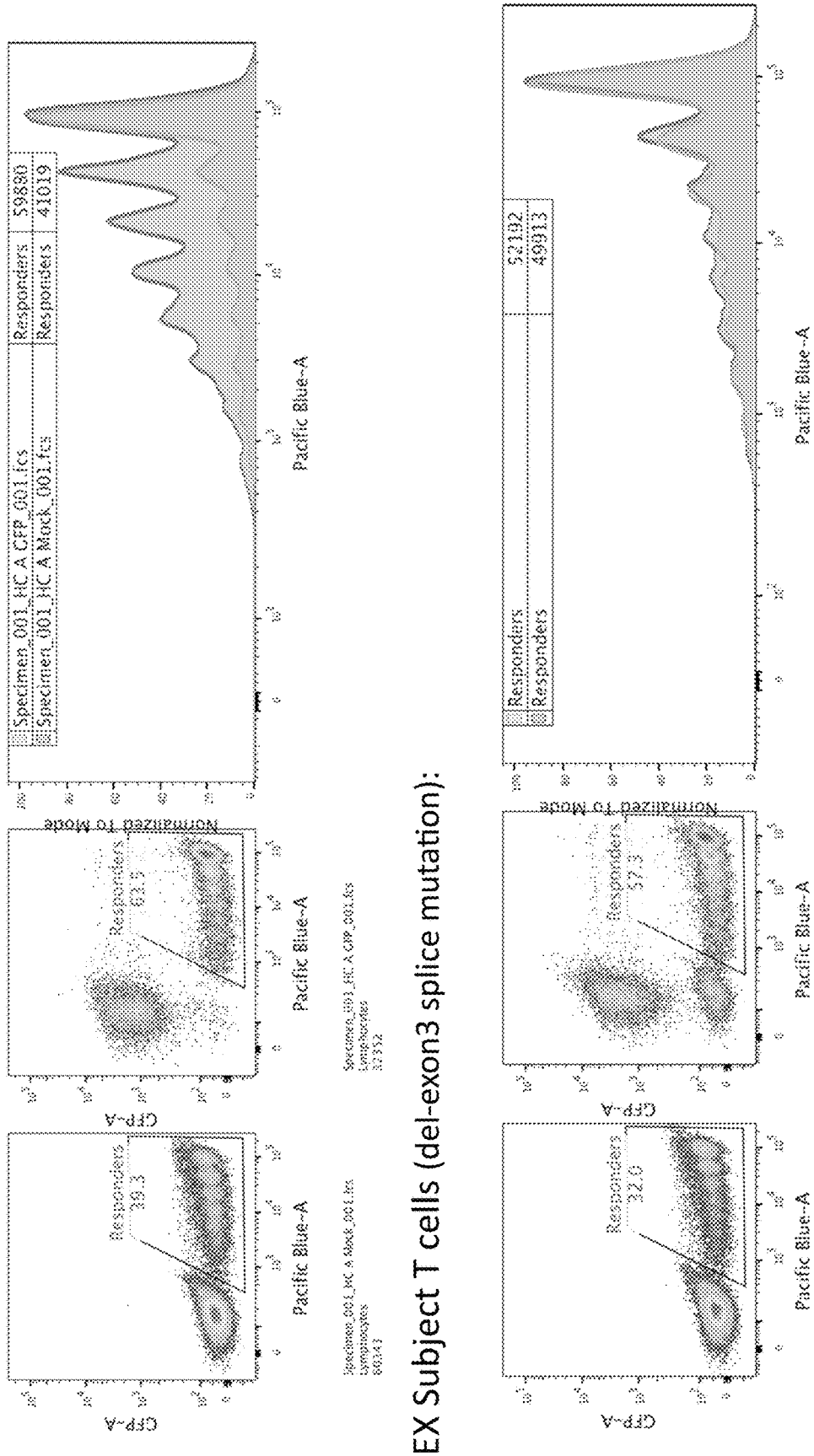
FIG. 18: Edited Cell Functional Activity: Lack of suppression of Teff proliferation using edited T cells from IPEX subject. Using same assay as FIG. 17, normal patient control cells or IPEX patient cells were mock edited or edited to enforce expression of the native FOXP3 gene. Incubation of edited healthy control cells with responders suppressed CFSE dilution of responders relative to mock edited cells, whereas incubation of edited IPEX patient cells showed no suppression of proliferation relative to mock edited cells.

Shown in FIG. 18, edited Cell Functional Activity: Lack of suppression of Teff proliferation using edited T cells from IPEX subject. Using same assay as FIG. 17, normal patient control cells or IPEX patient cells were mock edited or edited to enforce expression of the native FOXP3 gene. Incubation of edited healthy control cells with responders suppressed CFSE dilution of responders relative to mock edited cells, whereas incubation of edited IPEX patient cells showed no suppression of proliferation relative to mock edited cells.

Figure 19:
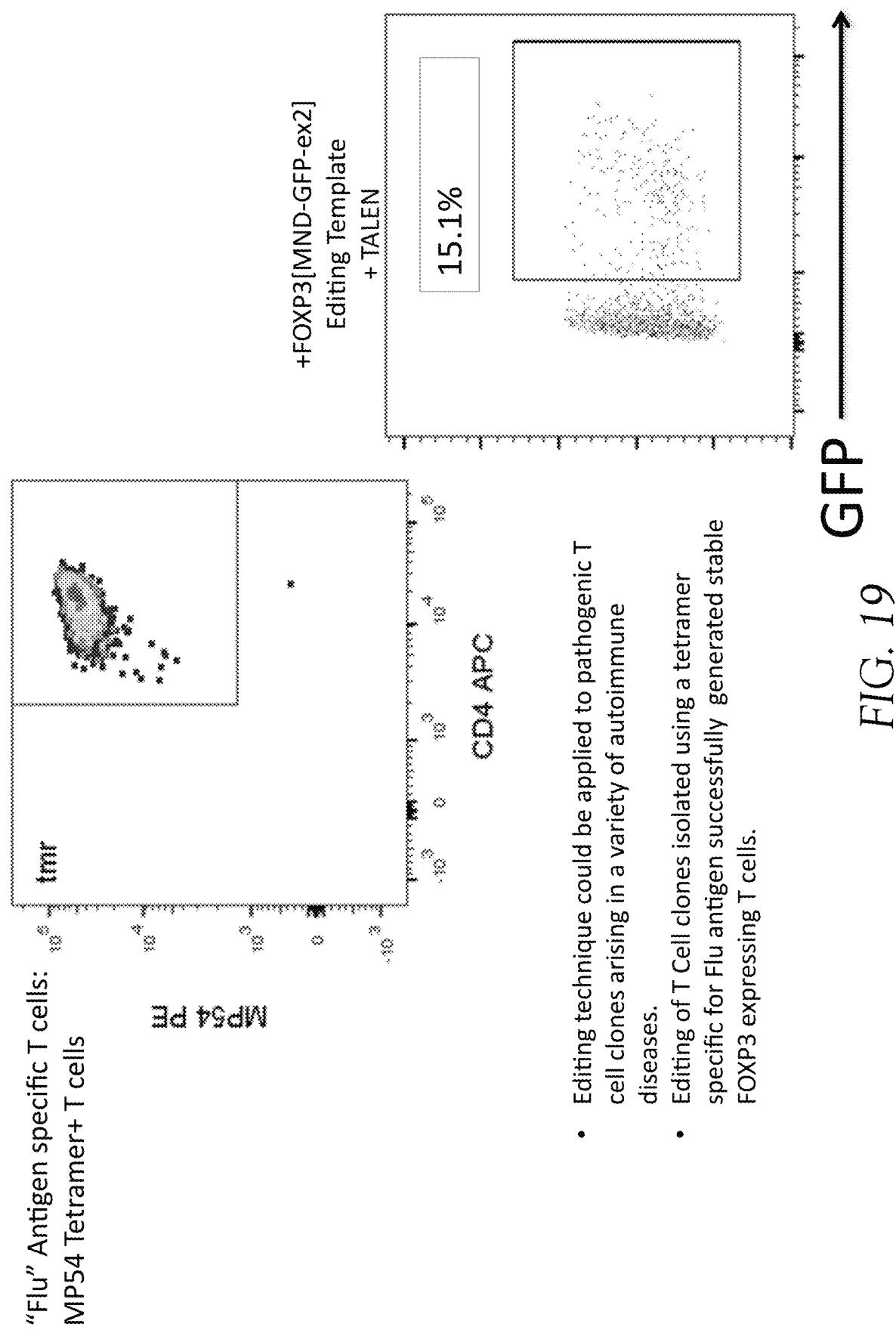
FIG. 19: Generation of Antigen specific $T_{reg}$-phenotype cells via FOXP3 gene editing. As shown, the editing techniques can be applied to pathogenic T cell clones that arise in a variety of autoimmune diseases. Editing of the T cell clones isolated using a tetramer specific for Flu antigen was shown to successfully generate stable FOXP3 expressing T cells.
Figure 20:
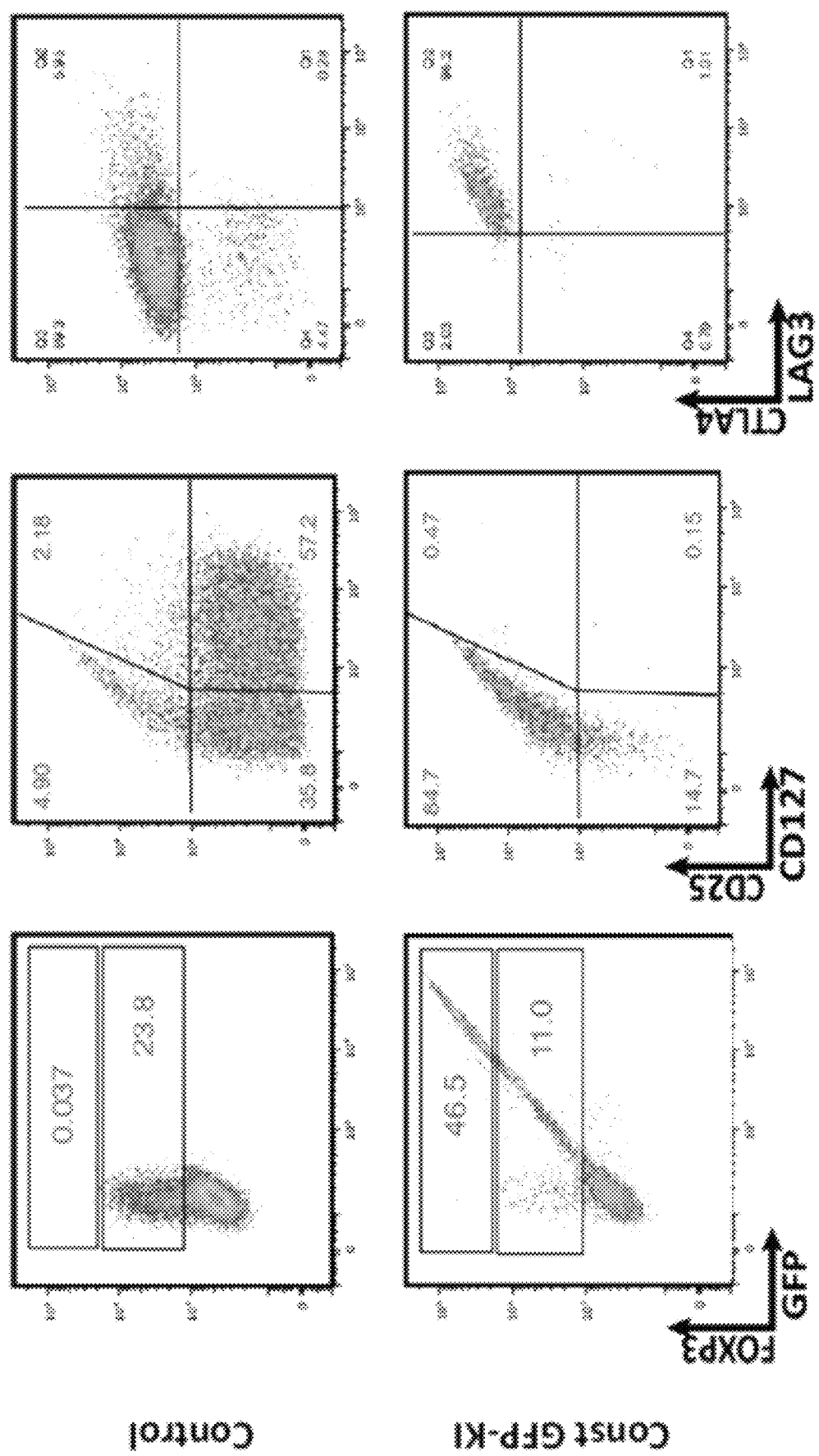
FIG. 20: Phenotype of Edited T Cells. As shown in the Figure, stable FOXP3 expressing T cells expressed CTLA4 and LAG3.

Antigen specific $T_{reg}$ cells were also generated via FOXP3 gene editing. As shown in FIG. 19, the editing techniques can be applied to pathogenic T cell clones that arise in a variety of autoimmune diseases. Editing of the T cell clones isolated using a tetramer specific for Flu antigen was shown to successfully generate stable FOXP3 expressing T cells.

As shown in these exemplary alternatives, edited cells can suppress Teff proliferation.

As some of the experiments provided herein are done in vitro, it is hard to predict that the same elevated levels of FOXP3 expression in cells can be maintained in in vivo tests, cells or subjects and that such elevated levels of FOXP3 expression in cells will be sufficient to ameliorate a pathogenic T-cell and/or B-cell response in an autoimmune disorder or GVHD, for example. It is also difficult to predict that the cells will have T regulatory cell characteristics in vivo. As such it may be advantageous for cells used for treatment, amelioration, or inhibition to be monitored in a subject to determine if the cells are maintained, increased or decreased before, during and/or after treatment. Methods to examine subjects for engineered cells after administration are known to those skilled in the art. For example, commercially available technology through Adaptive Biotechnologies and others is a system to sequence B and T cells to detect specific types of immune cells, such as an engineered cell or pathogenic B- or T-cell to determine if the cell is maintained, increased or decreased. As the cells may have been edited at different distances upstream from a coding exon, this may affect the expression of FOXP3 in vivo, as such the in vivo data does not predict the outcome in in vivo experiments. Furthermore, the use of different promotors, effector domains and activation domains may have a different outcome.

In some alternatives, of the methods of treatments, amelioration, or inhibition described herein, the methods further comprises monitoring the subject to determine if the engineered cells are maintained, increased or decreased before, during and/or after receiving the cells. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject.

The engineered cells would also have to be tested to see if they have an effect on T effector cells in vivo, as the in vitro experiments cannot be used to predict their effect on T effector cells in vivo or if they suppress the T effector cells.

CONCLUSION

Gene editing in primary human T cells permits enforced Foxp3 expression via introduction of a strong promoter and results in a stable $T_{reg}$ phenotype. Gene editing in CD4+ T cells is efficient and results in high, stable expression of Foxp3. Gene expression was also shown to be restricted to the endogenous gene locus. Edited cells demonstrate $T_{reg}$ functional properties (pSTAT5 & intracellular cytokine production), surface phenotype and in vitro function ($T_{effector}$ suppression). FOXP3 editing is feasible using antigen-specific T cells. Successful establishment of GVHD murine model will permit expanded in vivo functional testing of FOXP3 edited T cells.

Alternative 4: Phenotype and Function of Edited GFP FOXP3 Cells

Figure 21:
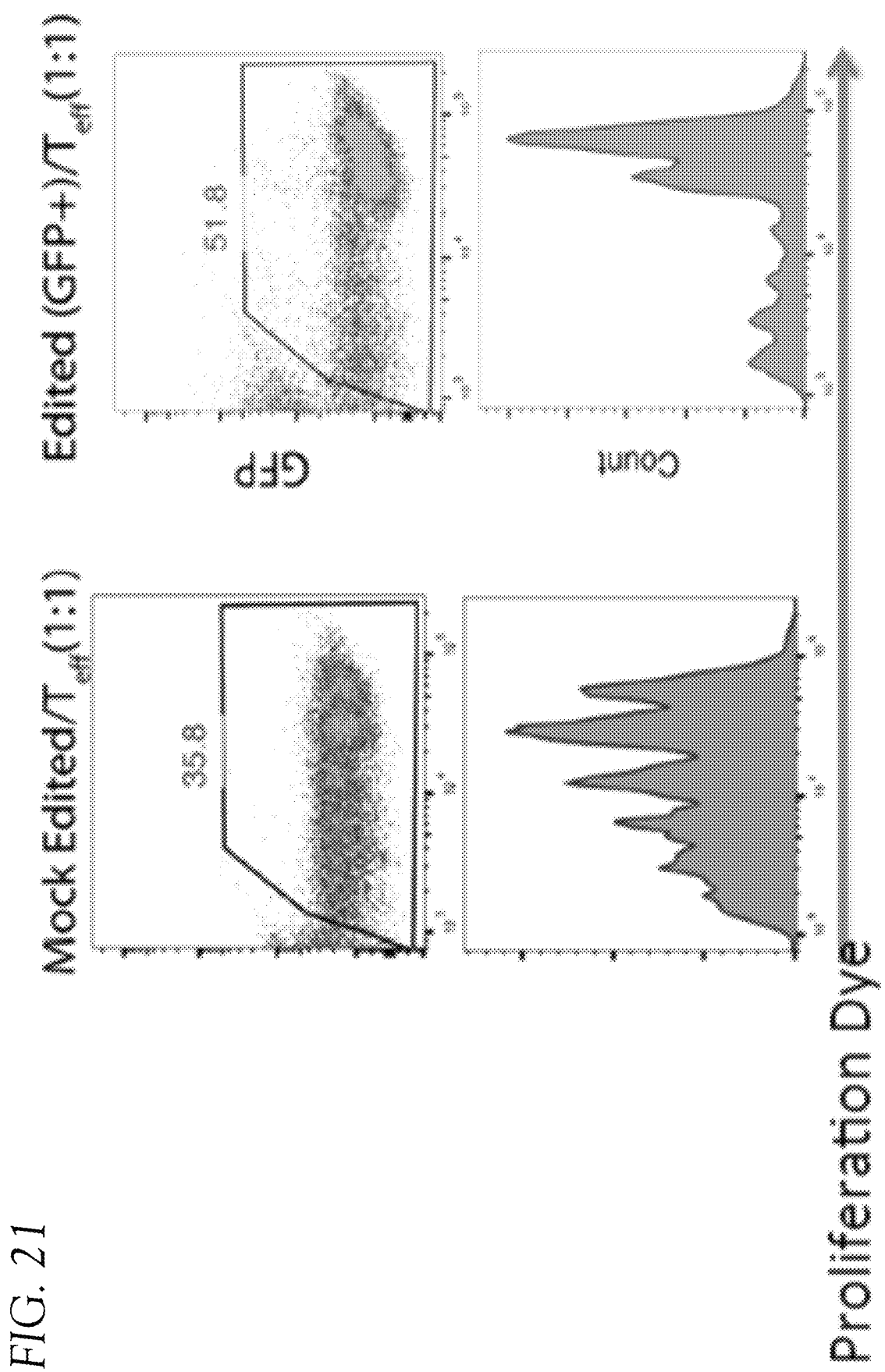
FIG. 21: Phenotype and function of edited GFP-FOXP3 T Cells. As shown the Figure, stable FOXP3 expressing T cells had a phenotype change (CD25+, CD45RO+, CCR7, and CD38/CTLA-4/LAP). The stable FOXP3 expressing T cells also show $T_{reg}$ like profile of intracellular cytokine expression (IL-2, IFN-γ and IL-4). pSTAT5 signaling was also sensitive to IL-2 when administered at 10 ng to 100 ng.

As shown in FIG. 21, stable FOXP3 expressing T cells had a phenotype change (CD25+, CD45RO+, CCR7, CD38/

CTLA-4/LAP). The stable FOXP3 expressing T cells also show $T_{reg}$ like profile of intracellular cytokine expression (IL-2, IFN-γ and IL-4). pSTAT5 signaling was also sensitive to IL-2 when administered at 10 ng to 100 ng. As such, stabile FOXP3 expressing T cells show a $T_{reg}$ like profile of intracellular cytokine expression.

As some of the experiments provided herein are done in vitro, it is hard to predict that the same elevated levels of FOXP3 expression in cells can be maintained in in vivo tests, cells or subjects and that such elevated levels of FOXP3 expression in cells will be sufficient to ameliorate a pathogenic T-cell and/or B-cell response in an autoimmune disorder or GVHD, for example. It is also difficult to predict that the cells will have T regulatory cell characteristics in vivo. As such, it may be advantageous for cells used for treatment, inhibition, or amelioration to be monitored in a subject to determine if the cells are maintained, increased or decreased before, during and/or after treatment. Methods to examine subjects for engineered cells after administration are known to those skilled in the art. For example, commercially available technology through Adaptive Biotechnologies and others is a system to sequence B and T cells to detect specific types of immune cells, such as an engineered cell or pathogenic B- or T-cell to determine if the cell is maintained, increased or decreased. As the cells may have been edited at different distances upstream from a coding exon, this may affect the expression of FOXP3 in vivo, as such the in vivo data does not predict the outcome in in vivo experiments. Furthermore, the use of different promotors, effector domains and activation domains may have a different outcome.

In some alternatives, of the methods of treatments, inhibition, or amelioration described herein, the methods further comprise monitoring the subject to determine if the engineered cells are maintained, increased or decreased before, during and/or after treatment. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject.

Alternative 5: In Vivo GVHD Experiments

Figure 22:
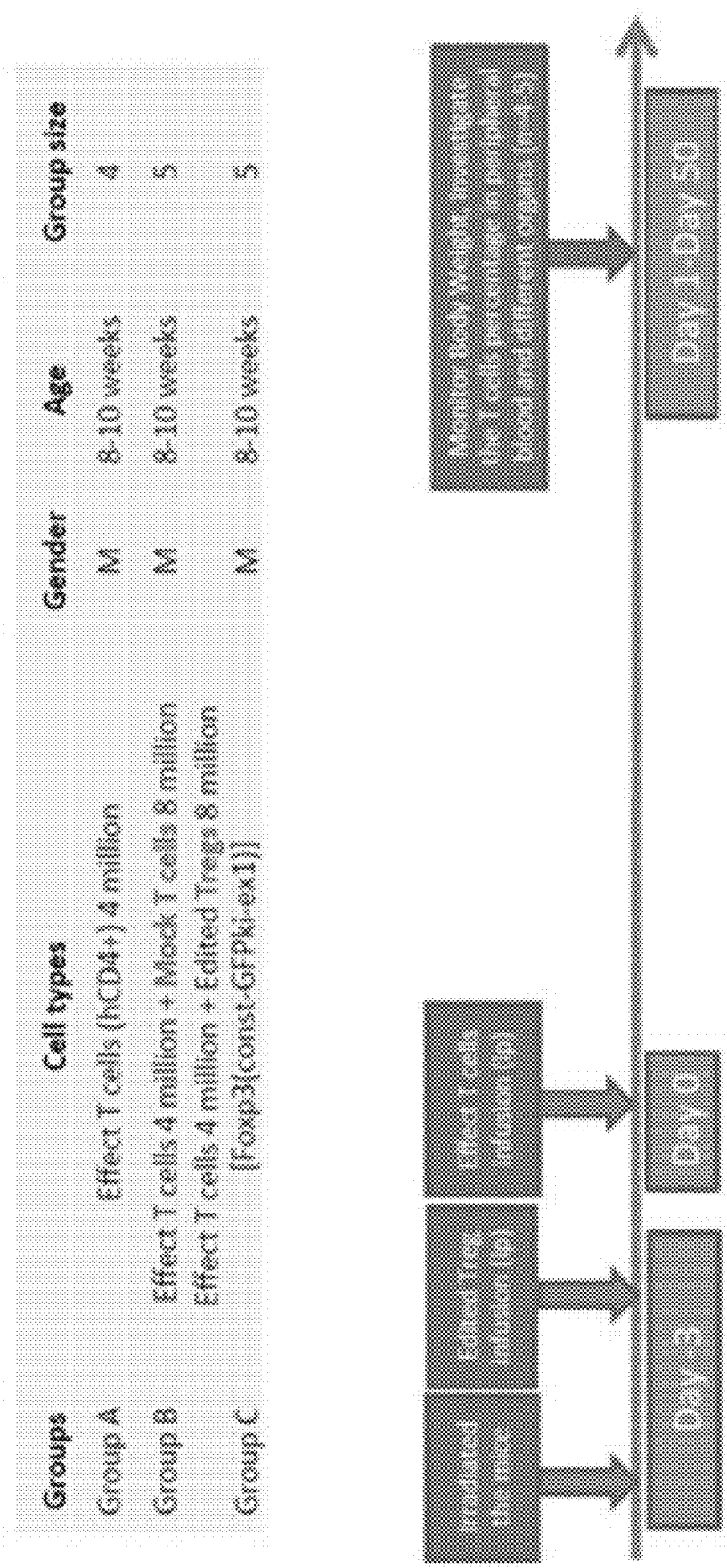
FIG. 22: in vivo GvHD experiments. As shown is the timeline for the preparation of the in vivo GvHD experiments. Mice are first irradiated to destroy the marrow cells. The engineered $T_{regs}$ stably expressing FOXP3 are then infused into the mice followed by an infusion of $T_{eff}$ cells. Between 1-50 days following the infusion, the mice are then monitored for body weight and investigated for the T cell percentages in the peripheral blood and in different organs.

Shown in FIG. 22, is the timeline for the preparation of the in vivo GvHD experiments. Mice are first irradiated to destroy the marrow cells. The engineered cells that have a $T_{regs}$ phenotype stably expressing FOXP3 are then infused into the mice followed by an infusion of $T_{eff}$ cells. Between 1-50 days following the infusion, the mice are then monitored for body weight and investigated for the T cell percentages in the peripheral blood and in different organs.

Figure 23:
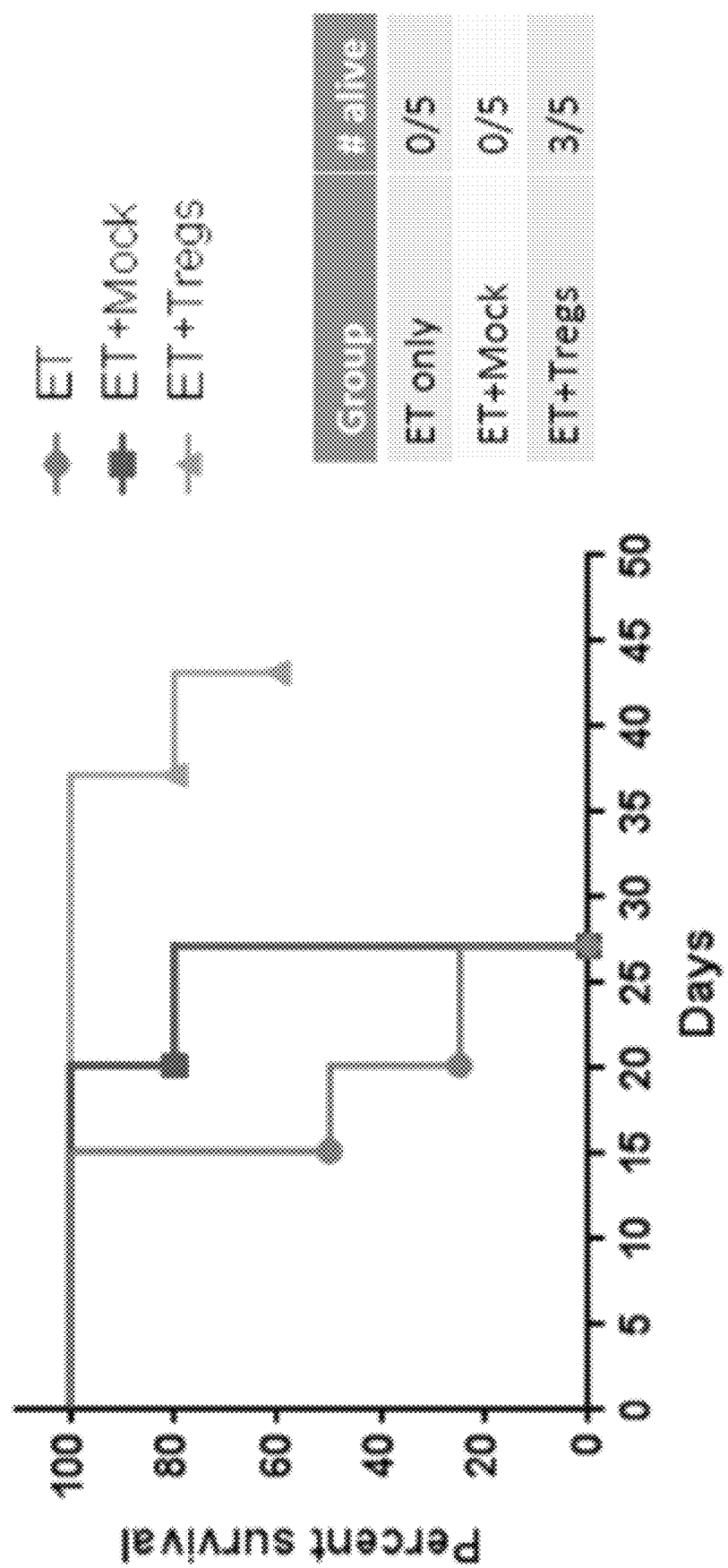
FIG. 23: in vivo GvHD experiments. As shown, the graph shows the percent survival of mice that received effector cells (ET, red circles), effector cells and mock edited T-cells (blue squares), and effectors cells and edited FOXP3 stabilized T-regs (Green triangles). Edited foxp3 stabilized Tregs produced a substantial survival advantage indicative of their capacity to ameliorate xenogeneic GvHD produced by the effector cells.

In FIG. 23, the graph shows the percent survival of mice that received effector cells (circles), effector cells and mock edited T-cells (squares), and effectors cells and edited FOXP3 stabilized cells that have T-regs phenotype (triangles). Edited foxp3 stabilized Tregs-phenotype cells produced a substantial survival advantage indicative of their capacity to ameliorate xenogeneic GvHD produced by the effector cells.

Figure 24:
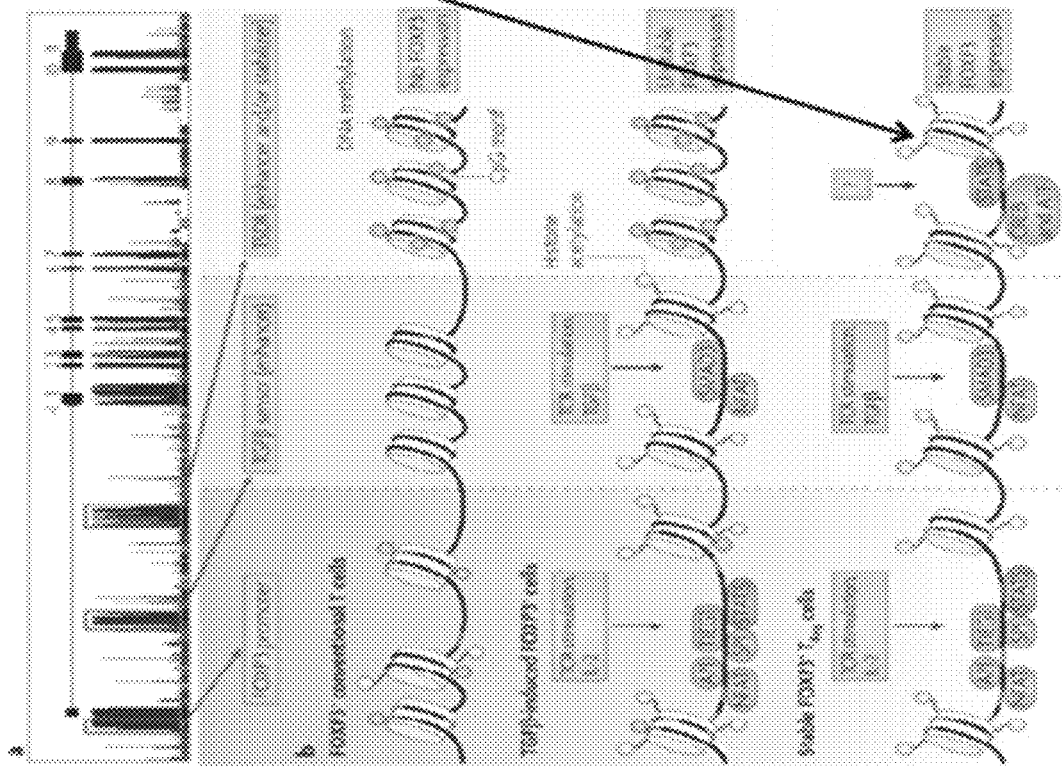
FIG. 24: TSDR CpG Methylation in Edited T Cells. Schematic of how the FOXP3 gene is regulated by methylation of regulatory regions upstream from first coding exon (actual exon 2).

Alternative 6: Molecular Similarities/Differences of Engineered Tolerogenic T Cells to Natural Thymic $T_{regs}$ Shown in FIG. 24 is the schematic of TSDR CpG Methylation in Edited T Cells. The FOXP3 gene is regulated by methylation of regulatory regions upstream from first coding exon (actual exon 2).

Figure 25:
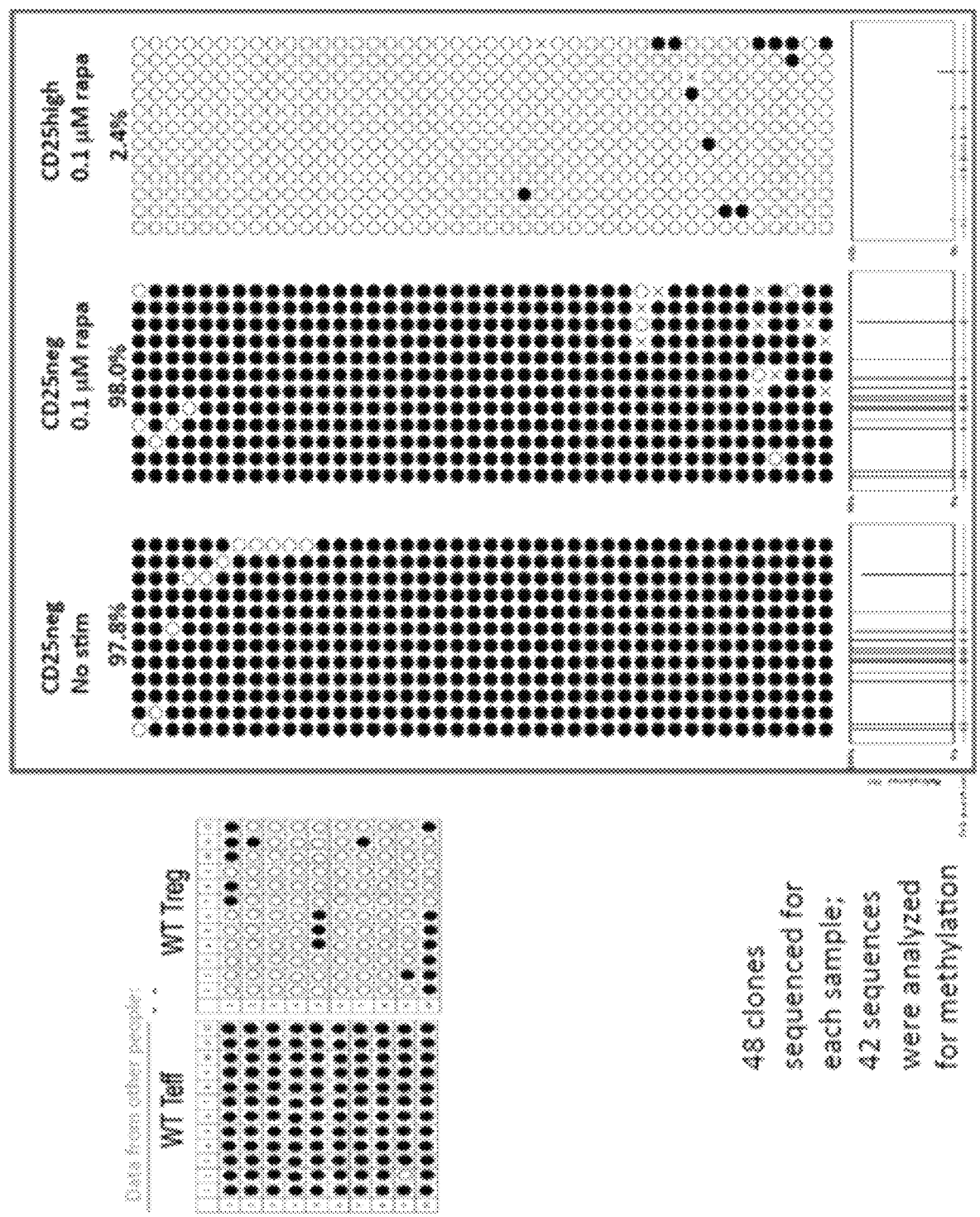
FIG. 25: Clones analyzed for methylation. Each black dot indicates a methylated CpG dinucleotide in a PCR fragment spanning the TSDR of a T-cell clone. As can be seen, CD25 negative cells have highly methylated TSDR's, indicative of closed, inactive, non-expressed FOXP3 locus, whereas CD25 high cells (natural Tregs) show nearly uniformly fully demethylated TSDR's.

The clones were then analyzed for methylation (FIG. 25). Each black dot indicates a methylated CpG dinucleotide in a PCR fragment spanning the TSDR of a T-cell clone. As can be seen, CD25 negative cells have highly methylated TSDR's, indicative of closed, inactive, non-expressed FOXP3 locus, whereas CD25 high cells (natural Tregs) show nearly uniformly fully demethylated TSDR's.

Figure 26:
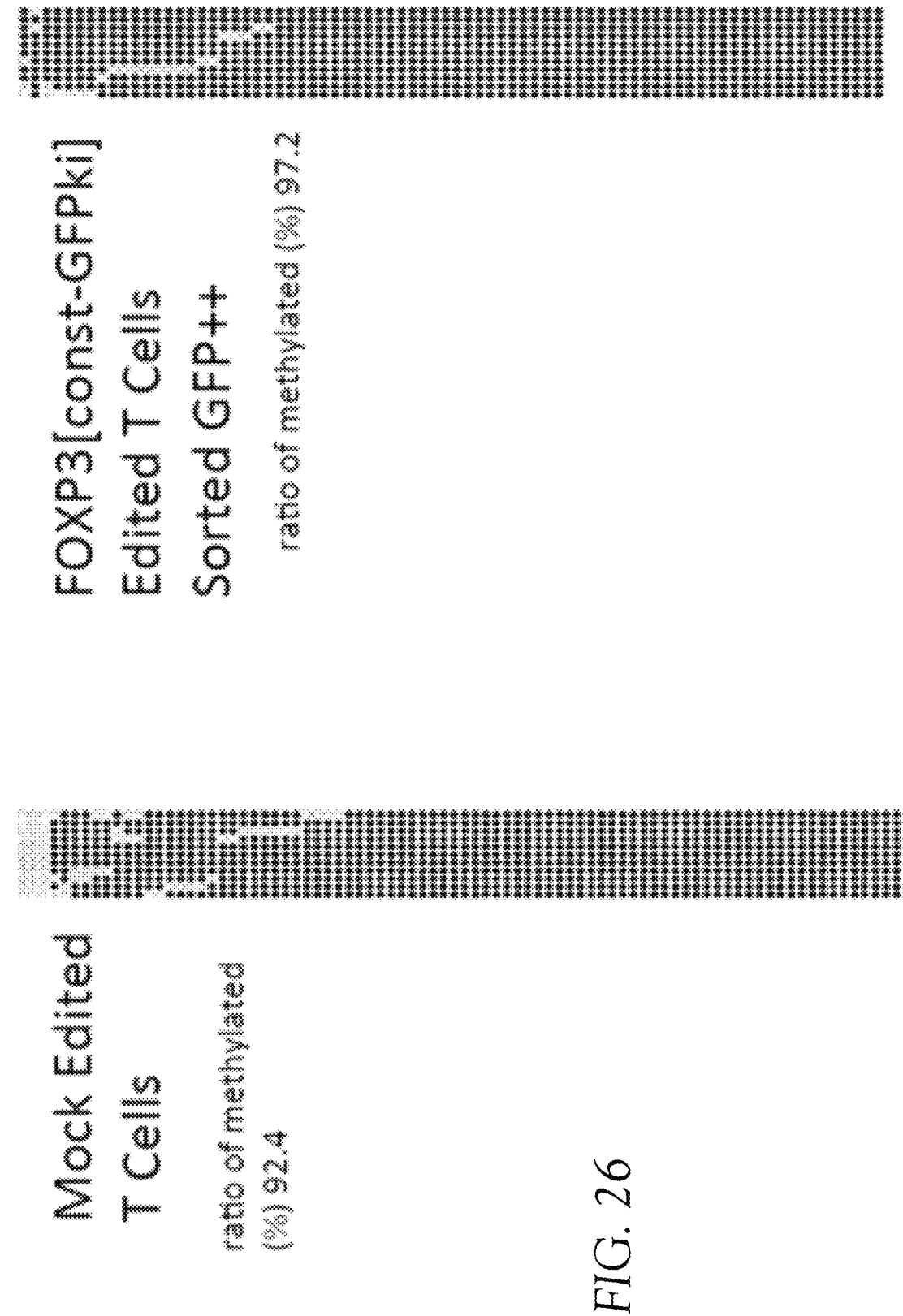
FIG. 26: TSDR methylation in edited T cells. Edited T-cells show fully methylated TSDR's, despite known high level FOXP3 expression, demonstrating that integration of a promoter downstream of the TSDR effectively bypasses the normal epigenetic regulation of the FOXP3 locus.

Edited T-cells show fully methylated TSDR's, despite known high level FOXP3 expression, demonstrating that integration of a promoter downstream of the TSDR effectively bypasses the normal epigenetic regulation of the FOXP3 locus (FIG. 26).

As some of the experiments provided herein are done in vitro, it is hard to predict that the same elevated levels of FOXP3 expression in cells can be maintained in in vivo tests, cells or subjects and that such elevated levels of FOXP3 expression in cells will be sufficient to ameliorate a pathogenic T-cell and/or B-cell response in an autoimmune disorder or GVHD, for example. It is also difficult to predict that the cells will have T regulatory cell characteristics in vivo. As such it may be advantageous for cells used for treatment, inhibition, or amelioration to be monitored in a subject to determine if the cells are maintained, increased or decreased before, during and/or after treatment. Methods to examine subjects for engineered cells after administration are known to those skilled in the art. For example, commercially available technology through Adaptive Biotechnologies and others is a system to sequence B and T cells to detect specific types of immune cells, such as an engineered cell or pathogenic B- or T-cell to determine if the cell is maintained, increased or decreased. As the cells may have been edited at different distances upstream from a coding exon, this may affect the expression of FOXP3 in vivo, as such the in vivo data does not predict the outcome in in vivo experiments. Furthermore, the use of different promotors, effector domains and activation domains may have a different outcome.

Methods of Making the Nucleic Acid

In some alternatives, a method of making a nucleic acid that bypasses epigenetic control of protein expression is provided. In some alternatives, the protein is FOXP3. In some alternatives, a method of making a nucleic acid for expression of FOXP3 is provided. The method comprises providing a first nucleotide sequence, wherein the first nucleotide sequence comprises a coding strand, the coding strand comprising one or more regulatory elements and a FOXP3 gene or portion thereof, providing a nuclease and performing a gene editing process on the first nucleotide sequence, which edits said one or more regulatory elements, and optionally edits the FOXP3 gene or portion thereof. In some alternatives, the first nucleotide sequence comprises a targeted locus. In some alternatives, the first targeted locus comprises a first coding exon. In some alternatives, the targeted locus comprises a first coding exon following completion of the gene editing process. In some alternatives, the targeted locus is at the one or more regulatory elements. In some alternatives, the targeted locus is at the FOXP3 gene or portion thereof, wherein the FOXP3 gene or portion thereof comprises the first coding exon. In some alternatives, the nuclease is Cas9, a zinc-finger nuclease or TALEN. In some alternatives, the gene editing process is a gene knock-in process for insertion of a heterologous promoter, a heterologous transcriptional enhancer domain or both. In some alternatives, the heterologous promoter is a constitutive promoter. In some alternatives, the promoter is an EF1 alpha promoter, a PGK promoter, or an MND promoter. In some alternatives, the promoter is a heterologous weak promoter (e.g., a promoter having less activity or transcriptional efficiency than the endogenous promoter and/or a constitutive promoter). In some alternatives, the promoter is an inducible promoter. In some alternatives, the inducible promoter is inducible by a drug or a steroid. In some alternatives, the method further comprises insertion of one or more heterologous transcriptional enhancer domains. In some alternatives, the method further comprises insertion of one or more heterologous transcriptional activation domains. In some alternatives, the method further comprises insertion of a ubiquitous chromatin opening element (UCOE). In some alternatives, the method further comprises insertion of an inducible effector. In some alternatives, the inducible effector is inducible by a steroid or a drug. In some alternatives, the heterologous promoter is inserted anywhere upstream from the first coding exon on the coding strand, wherein the first coding exon represents an exon following completion of the gene editing process and wherein the coding strand further comprises a start codon of the FOXP3 gene. In some alternatives, the heterologous promoter is inserted downstream from the one or more regulatory elements on the coding strand. In some alternatives, the method further comprises genetically modifying the one or more regulatory elements.

Nucleic Acids for Stable Expression of FOXP3

In some alternatives, a nucleic acid for bypassing epigenetic control for expression of a protein is provided. In some alternatives, the protein is FOXP3. In some alternatives, a nucleic acid is provided, wherein the nucleic acid comprises a coding strand that comprises heterologous regulatory elements and a heterologous promoter, which are operably linked to a FOXP3 gene or portion thereof, wherein the FOXP3 gene or portion thereof comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the promoter is an inducible promoter. In some alternatives, the inducible promoter is inducible by a drug or a steroid. In some alternatives, the heterologous promoter is inserted upstream from the first coding exon. In some alternatives, the nucleic acid further comprises one or more heterologous transcriptional enhancer domains. In some alternatives, the nucleic acid further comprises one or more heterologous transcriptional activation domains. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified.

Methods of Making a Genetically Engineered Cell for Stable Expression of a Protein In some alternatives, a method of making a genetically engineered cell that bypasses epigenetic control is provided. In some alternatives, a method of making a genetically engineered cell is provided, the method comprising providing a cell, wherein the cell comprises a first nucleotide sequence, wherein the first nucleotide sequence comprises a coding strand, the coding strand comprising one or more regulatory elements and a FOXP3 gene or portion thereof, providing a second nucleotide sequence encoding a nuclease or providing a protein nuclease and introducing the second oligonucleotide or protein nuclease into the cell for genetic modification. In some alternatives, the genetic modification is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus is at the first coding exon. In some alternatives, the targeted locus is within 10, 20, 30, 40, 50, 60, 70, 80, 90, 100 or 110 base pairs upstream of the first coding exon or any number of base pairs within a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of one or more heterologous enhancer domains into the first nucleotide sequence. In some alternatives, the method further comprises insertion of one or more heterologous transcriptional activation domains into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand or upstream from the synthetic first coding exon that is created through completion of the gene editing process. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

Cells

In some alternatives, a genetically engineered cell for bypassing epigenetic control for expression of a protein is provided. In some alternatives, the protein is FOXP3. In some alternatives, a genetically engineered cell for the expression of FOXP3, manufactured by the method of any one of the methods described herein is provided. The method comprises providing a cell, wherein the cell comprises a first nucleotide sequence, wherein the first nucleotide sequence comprises a coding strand, the coding strand comprising one or more regulatory elements and a FOXP3 gene or portion thereof, providing a second nucleotide sequence encoding a nuclease or providing a protein nuclease and introducing the second oligonucleotide or protein nuclease into the cell for genetic modification. In some alternatives, the genetic modification is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus is at the first coding exon. In some alternatives, the targeted locus is within 10, 20, 30, 40, 50, 60, 70, 80, 90, 100 or 110 base pairs upstream of the first coding exon or any number of base pairs within a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of one or more heterologous enhancer domains into the first nucleotide sequence. In some alternatives, the method further comprises insertion of one or more heterologous transcriptional activation domains into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand or upstream from the synthetic first coding exon that is created through completion of the gene editing process. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In some alternatives, a genetically engineered cell for the expression of FOXP3 is provided, wherein the genetically engineered cell comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises one or more heterologous transcriptional enhancer domains. In some alternatives, the nucleic acid further comprises one or more a heterologous transcriptional activation domains. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the cells can be engineered to express a chimeric antigen receptor.

Compositions

The disclosure provides methods of making uses or methods of using these compositions for performing cellular immunotherapy in a subject having a disease or disorder. In some alternatives, the composition comprises the genetically engineered cell of any one or more of the cells of any of the alternatives herein and a pharmaceutical excipient. The cell is a genetically engineered cell for the expression of FOXP3, manufactured by the method of any one of the methods described herein is provided. The method comprises providing a cell, wherein the cell comprises a first nucleotide sequence, wherein the first nucleotide sequence comprises a coding strand, the coding strand comprising one or more regulatory elements and a FOXP3 gene or portion thereof, providing a second nucleotide sequence encoding a nuclease or providing a protein nuclease and introducing the second oligonucleotide or protein nuclease into the cell for genetic modification. In some alternatives, the genetic modification is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus is at the first coding exon. In some alternatives, the targeted locus is within 10, 20, 30, 40, 50, 60, 70, 80, 90, 100 or 110 base pairs upstream of the first coding exon or any number of base pairs within a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of one or more heterologous enhancer domains into the first nucleotide sequence. In some alternatives, the method further comprises insertion of one or more heterologous transcriptional activation domains into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand or upstream from the synthetic first coding exon that is created through completion of the gene editing process. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In some alternatives, the genetically engineered cell comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises one or more heterologous transcriptional enhancer domains. In some alternatives, the nucleic acid further comprises one or more heterologous transcriptional activation domains. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the cells can be engineered to express a chimeric antigen receptor.

Methods of Treatment or Amelioration

In some alternatives, a method of treating, inhibiting, or ameliorating an autoimmune disorder in a subject is provided, the method comprising administering to the subject the genetically modified cell of any one of more of the cells of any one of the alternatives provided herein or the composition of any one of the alternatives provided herein. In some alternatives, the composition comprises the genetically engineered cell of any one or more of the cells of any of the alternatives herein and a pharmaceutical excipient. The cell is a genetically engineered cell for the expression of FOXP3, manufactured by the method of any one of the methods described herein is provided. The method comprises providing a cell, wherein the cell comprises a first nucleotide sequence, wherein the first nucleotide sequence comprises a coding strand, the coding strand comprising one or more regulatory elements and a FOXP3 gene or portion thereof, providing a second nucleotide sequence encoding a nuclease or providing a protein nuclease and introducing the second oligonucleotide or protein nuclease into the cell for genetic modification. In some alternatives, the genetic modification is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus is at the first coding exon. In some alternatives, the targeted locus is within 10, 20, 30, 40, 50, 60, 70, 80, 90, 100 or 110 base pairs upstream of the first coding exon or any number of base pairs within a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of one or more heterologous enhancer domains into the first nucleotide sequence. In some alternatives, the method further comprises insertion of one or more heterologous transcriptional activation domains into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand or upstream from the synthetic first coding exon that is created through completion of the gene editing process. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In some alternatives, the genetically engineered cell comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises one or more heterologous transcriptional enhancer domains. In some alternatives, the nucleic acid further comprises one or more heterologous transcriptional activation domains. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell, the cell is a T-regulatory cell. In some alternatives, the cells can be engineered to express a chimeric antigen receptor. In some alternatives, the autoimmune disease is rheumatoid arthritis, diabetes, inflammatory bowel disease, IPEX, immune dysregulation, polyendocrinopathy, enteropathy, X-linked (IPEX) syndrome, Crohn's disease, multiple sclerosis, idiopathic or systemic lupus erythematosus. In some alternatives, the autoimmune disease is systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease and/or Ataxia-telangiectasia. In some alternatives, the autoimmune disorder is systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease, IPEX, Immune dysregulation, polyendocrinopathy, enteropathy, X-linked (IPEX) syndrome and/or Ataxia-telangiectasia. In some alternatives, the subject is identified or selected to receive therapy for an autoimmune disease. In some alternatives, the subject is refractory to standard therapies for autoimmune disease or standard therapies for anti-inflammatory therapies. Such identification or selection can be accomplished based on clinical or diagnostic evaluation.

In some alternatives, the subject is given a combination therapy, which the subject is administered anti-rejection drugs or anti-inflammatory drugs in combination with the engineered cells. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the anti-inflammatory drugs comprise Tysabri®, steroids, ammunosuppressants, NSAID's, immunoglobulins, paracetramol, celecoxib, indomethacin or diclofenac. In some alternatives, the subject is monitored for changes in the engineered T cells expressing FOxp3+, and the populations of engineered cells that express a Treg phenotype or pathogenic T- or B-cells populations in vivo before, during and/or after the course of receiving the cells. In some alternatives, the subject is selected to receive another administration of engineered cells depending to the first response to a first bolus of cells. In some alternatives, the subject is administered another dose of cells within 1 week, 2 weeks or one month from the initial dose.

In some alternatives, of the methods of treatments described herein, the methods further comprise monitoring the subject to determine if the engineered cells are maintained, increased or decreased before, during and/or after treatment. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject.

In some alternatives, a method of treating, inhibiting, or ameliorating side effects of organ transplantation in a subject is provided, the method comprising administering to the subject the genetically modified cell of any one of more of the cells of any one of the alternatives herein or the composition of any one of the alternatives herein. In some alternatives, the composition comprises the genetically engineered cell of any one or more of the cells of any of the alternatives herein and a pharmaceutical excipient. The cell is a genetically engineered cell for the expression of FOXP3, manufactured by the method of any one of the methods described herein is provided. The method comprises providing a cell, wherein the cell comprises a first nucleotide sequence, wherein the first nucleotide sequence comprises a coding strand, the coding strand comprising one or more regulatory elements and a FOXP3 gene or portion thereof, providing a second nucleotide sequence encoding a nuclease or providing a protein nuclease and introducing the second oligonucleotide or protein nuclease into the cell for genetic modification. In some alternatives, the genetic modification is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus is at the first coding exon. In some alternatives, the targeted locus is within 10, 20, 30, 40, 50, 60, 70, 80, 90, 100 or 110 base pairs upstream of the first coding exon or any number of base pairs within a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of one or more heterologous enhancer domains into the first nucleotide sequence. In some alternatives, the method further comprises insertion of one or more heterologous transcriptional activation domains into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand or upstream from the synthetic first coding exon that is created through completion of the gene editing process. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

In some alternatives, the genetically engineered cell comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises one or more heterologous transcriptional enhancer domains. In some alternatives, the nucleic acid further comprises one or more heterologous transcriptional activation domains. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In some alternatives, a method of treating, inhibiting, or ameliorating side effects of organ transplantation in a subject, such as organ rejection is provided, the method comprising administering to the subject the genetically modified cell of any one of more of the cells of any one of the alternatives herein or the composition of any one of the alternatives herein. In some alternatives, the composition comprises the genetically engineered cell of any one or more of the cells of any of the alternatives herein and a pharmaceutical excipient. The cell is a genetically engineered cell for the expression of FOXP3, manufactured by the method of any one of the methods described herein is provided. The method comprises providing a cell, wherein the cell comprises a first nucleotide sequence, wherein the first nucleotide sequence comprises a coding strand, the coding strand comprising one or more regulatory elements and a FOXP3 gene or portion thereof, providing a second nucleotide sequence encoding a nuclease or providing a protein nuclease and introducing the second oligonucleotide or protein nuclease into the cell for genetic modification. In some alternatives, the genetic modification is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus is at the first coding exon. In some alternatives, the targeted locus is within 10, 20, 30, 40, 50, 60, 70, 80, 90, 100 or 110 base pairs upstream of the first coding exon or any number of base pairs within a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of one or more heterologous enhancer domains into the first nucleotide sequence. In some alternatives, the method further comprises insertion of one or more heterologous transcriptional activation domains into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand or upstream from the synthetic first coding exon that is created through completion of the gene editing process. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

In some alternatives, the genetically engineered cell comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter having less activity or transcriptional efficiency than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises one or more heterologous transcriptional enhancer domains. In some alternatives, the nucleic acid further comprises one or more heterologous transcriptional activation domains. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, of the methods of treatments, inhibitions, or ameliorations described herein, the methods further comprise monitoring the subject to determine if the engineered cells are maintained, increased or decreased before, during and/or after receiving the cells. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject.

In some alternatives, a method of treating, inhibiting, or ameliorating an autoimmune disorder in a subject is provided, the method comprising withdrawing cells from the subject in need, wherein the cells comprise a first nucleotide sequence, wherein the first nucleotide sequence comprises a coding strand, the coding strand comprising one or more regulatory elements a FOXP3 gene or portion thereof, wherein the FOXP3 gene or portion thereof comprises a first coding exon providing a second nucleotide sequence encoding a nuclease or providing a protein nuclease introducing the second nucleotide sequence or protein nuclease into the cell for genetic modification, wherein the genetic modification is a gene knock-in process for insertion of a promoter into the first nucleotide sequence and introducing the cell into the subject for treatment, inhibition, or amelioration. In some alternatives, the autoimmune disease is rheumatoid arthritis, diabetes, inflammatory bowel disease, IPEX, immune dysregulation, polyendocrinopathy, enteropathy, X-linked (IPEX) syndrome, Crohn's disease, multiple sclerosis, idiopathic or systemic lupus erythematosus. In some alternatives, the autoimmune disease is systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease and/or Ataxia-telangiectasia. In some alternatives, the subject is identified or selected to receive therapy for an autoimmune disease. In some alternatives, the autoimmune disease is rheumatoid arthritis, diabetes, inflammatory bowel disease, IPEX, immune dysregulation, polyendocrinopathy, enteropathy, X-linked (IPEX) syndrome, Crohn's disease, multiple sclerosis, idiopathic or systemic lupus erythematosus. Such identification or selection can be accomplished by diagnostic and/or clinical evaluation. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

In some alternatives, a method of treating, inhibiting, or ameliorating side effects of organ transplantation in a subject is provided, the method comprising withdrawing cells from the subject in need, wherein the cells comprise a first nucleotide sequence, wherein the first nucleotide sequence comprises a coding strand, the coding strand comprising one or more regulatory elements, a FOXP3 gene or portion thereof, wherein the FOXP3 gene or portion thereof comprises a first coding exon, providing a second nucleotide sequence encoding a nuclease or providing a protein nuclease, introducing the second nucleotide sequence or protein nuclease into the cell for genetic modification, wherein the genetic modification is a gene knock-in process for insertion of a promoter into the first nucleotide sequence and introducing the cell into the subject for treatment, inhibition, or amelioration. In some alternatives, of the methods of treatments, inhibitions, or ameliorations described herein, the methods further comprise monitoring the subject to determine if the engineered cells are maintained, increased or decreased before, during and/or after receiving the cells. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

In some alternatives, a method of treating, inhibiting, or ameliorating side effects of organ transplantation in a subject, such as organ rejection is provided, the method comprising withdrawing cells from the subject in need, wherein the cells comprise a first nucleotide sequence, wherein the first nucleotide sequence comprises a coding strand, the coding strand comprising, one or more regulatory elements, a FOXP3 gene or portion thereof, wherein the FOXP3 gene or portion thereof comprises a first coding exon, providing a second nucleotide sequence encoding a nuclease or providing a protein nuclease, introducing the second nucleotide sequence or protein nuclease into the cell for genetic modification, wherein the genetic modification is a gene knock-in process for insertion of a promoter into the first nucleotide sequence and introducing the cell into the subject for treatment. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

More Alternatives

In some alternatives, a method of making a nucleic acid for expression of FOXP3 is provided, wherein the method comprises providing a first nucleotide sequence, wherein the first nucleotide sequence comprises a coding strand, the coding strand comprising one or more regulatory elements and a FOXP3 gene or portion thereof, providing a nuclease and performing a gene editing process on the first nucleotide sequence, which edits said one or more regulatory elements, and optionally edits the FOXP3 gene or portion thereof. In some alternatives, the first nucleotide sequence comprises a targeted locus. In some alternatives, the targeted locus comprises a natural first coding exon. In some alternatives, completion of the gene editing process results in a first coding exon in the targeting locus following the gene editing process. In some alternatives, the targeted locus is at the one or more regulatory elements. In some alternatives, the targeted locus is at the FOXP3 gene or portion thereof. In some alternatives, the FOXP3 gene or portion thereof comprises the first natural coding exon In some alternatives, the nuclease is Cas9, a zinc-finger nuclease or TALEN. In some alternatives, the gene editing process is a gene knock-in process for insertion of a heterologous promoter, a heterologous transcriptional enhancer domain or both. In some alternatives, the heterologous promoter is a constitutive promoter. In some alternatives, the promoter is an EF1 alpha promoter, a PGK promoter, or an MND promoter. In some alternatives, the promoter is a heterologous weak promoter (e.g., a promoter that generates less expression than the endogenous promoter and/or a constitutive promoter). In some alternatives, the promoter is an inducible promoter. In some alternatives, the inducible promoter is inducible by a drug or a steroid. In some alternatives, the method further comprises insertion of a heterologous transcriptional enhancer domain, wherein the enhancer domain is upstream or downstream from the one or more regulatory sequences. In some alternatives, the method further comprises insertion of a heterologous transcriptional activation domain. In some alternatives, the method further comprises insertion of a ubiquitous chromatin opening element (UCOE). In some alternatives, the method further comprises insertion of an inducible effector. In some alternatives, the inducible effector is inducible by a steroid or a drug. In some alternatives, the heterologous promoter is inserted, wherein insertion of the heterologous promoter generates the first coding exon wherein the heterologous promoter is at a position anywhere upstream from the first coding exon on the coding strand, and wherein the coding strand further comprises a start codon of the FOXP3 gene. In some alternatives, the heterologous promoter is inserted at a position anywhere upstream from the first natural exon on the coding strand, and wherein the coding strand further comprises a start codon of the FOXP3 gene. In some alternatives, the heterologous promoter is inserted downstream from the one or more regulatory elements on the coding strand. In some alternatives, the method further comprises genetically modifying the one or more regulatory elements.

In some alternatives, a nucleic acid for FOXP3 expression, made by any one of the methods of any one of the alternatives herein is provided. The method comprises providing a first nucleotide sequence, wherein the first nucleotide sequence comprises a coding strand, the coding strand comprising one or more regulatory elements and a FOXP3 gene or portion thereof, providing a nuclease and performing a gene editing process on the first nucleotide sequence, which edits said one or more regulatory elements, and optionally edits the FOXP3 gene or portion thereof. In some alternatives, the first nucleotide sequence comprises a targeted locus. In some alternatives, the targeted locus comprises a natural first coding exon. In some alternatives, completion of the gene editing process results in a first coding exon in the targeting locus following the gene editing process. In some alternatives, the targeted locus is at the one or more regulatory elements. In some alternatives, the targeted locus is at the FOXP3 gene or portion thereof. In some alternatives, the FOXP3 gene or portion thereof comprises the first natural coding exon In some alternatives, the nuclease is Cas9, a zinc-finger nuclease or TALEN. In some alternatives, the gene editing process is a gene knock-in process for insertion of a heterologous promoter, a heterologous transcriptional enhancer domain or both. In some alternatives, the heterologous promoter is a constitutive promoter. In some alternatives, the promoter is an EF1 alpha promoter, a PGK promoter, or an MND promoter. In some alternatives, the promoter is a heterologous weak promoter (e.g., a promoter that generates less expression than the endogenous promoter and/or a constitutive promoter). In some alternatives, the promoter is an inducible promoter. In some alternatives, the inducible promoter is inducible by a drug or a steroid. In some alternatives, the method further comprises insertion of a heterologous transcriptional enhancer domain, wherein the enhancer domain is upstream or downstream from the one or more regulatory sequences. In some alternatives, the method further comprises insertion of a heterologous transcriptional activation domain. In some alternatives, the method further comprises insertion of a ubiquitous chromatin opening element (UCOE). In some alternatives, the method further comprises insertion of an inducible effector. In some alternatives, the inducible effector is inducible by a steroid or a drug. In some alternatives, the heterologous promoter is inserted, wherein insertion of the heterologous promoter generates the first coding exon wherein the heterologous promoter is at a position anywhere upstream from the first coding exon on the coding strand, and wherein the coding strand further comprises a start codon of the FOXP3 gene. In some alternatives, the heterologous promoter is inserted at a position anywhere upstream from the first natural exon on the coding strand, and wherein the coding strand further comprises a start codon of the FOXP3 gene. In some alternatives, the heterologous promoter is inserted downstream from the one or more regulatory elements on the coding strand. In some alternatives, the method further comprises genetically modifying the one or more regulatory elements.

In some alternatives, a nucleic acid is provided, the nucleic acid comprising a coding strand that comprises heterologous regulatory elements and a heterologous promoter, which are operably linked to a FOXP3 gene or portion thereof, wherein the FOXP3 gene or portion thereof comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the promoter is an inducible promoter. In some alternatives, the inducible promoter is inducible by a drug or a steroid. In some alternatives, the heterologous promoter is at a position upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified.

In some alternatives, a method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In some alternatives, a genetically engineered cell for the expression of FOXP3, manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In some alternatives, a genetically engineered cell for the expression of FOXP3, the genetically engineered cell comprising a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In some alternatives, a composition comprising the genetically engineered cell of any one or more of the cells of any one of the alternatives herein and a pharmaceutical excipient is provided. The genetically engineered cell for the expression of FOXP3 can be manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the genetically engineered cell for the expression of FOXP3 comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell.

In some alternatives, a method of treating, inhibiting, or ameliorating an autoimmune disorder in a subject, the method comprising: administering to the subject the genetically modified cell of any one of more of the cells of any one of the alternatives herein or the composition of any one of the alternatives is provided. The composition comprising the genetically engineered cell of any one or more of the cells of any one of the alternatives herein and a pharmaceutical excipient is provided. The genetically engineered cell for the expression of FOXP3 can be manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the genetically engineered cell for the expression of FOXP3 comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the autoimmune disease is rheumatoid arthritis, diabetes, inflammatory bowel disease, IPEX, immune dysregulation, polyendocrinopathy, enteropathy, X-linked (IPEX) syndrome, Crohn's disease, multiple sclerosis, idiopathic or systemic lupus erythematosus. In some alternatives, the subject is identified or selected to receive therapy for an autoimmune disease. In some alternatives, the subject is given a combination therapy, which the subject is administered drugs for suppression of the autoimmune disease in combination with the engineered cells. In some alternatives, the subject is monitored for changes in FOXp3+Treg phenotype cell populations in vivo during the course of treatment. In some alternatives, the subject is selected to receive another administration of engineered cells. In some alternatives, the subject is given a combination therapy, which the subject is administered anti-rejection drugs or anti-inflammatory drugs in combination with the engineered cells. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the anti-inflammatory drugs comprise Tysabri®, steroids, ammunosuppressants, NSAID's, immunoglobulins, paracetramol, celecoxib, indomethacin or diclofenac. In some alternatives, the subject is monitored for changes in the engineered T cells expressing FOXp3+, and the populations of engineered cells that express a Treg phenotype or pathogenic T- or B-cells populations in vivo before, during and/or after the course of treatment, inhibition, or amelioration. In some alternatives, the subject is selected to receive another administration of engineered cells depending to the first response to treatment, inhibition, or amelioration. In some alternatives, the subject is administered another dose of cells within 1 week, 2 weeks or one month from the initial dose. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

In some alternatives, a method of treating, inhibiting, or ameliorating side effects of organ transplantation in a subject is provided, the method comprising: administering to the subject the genetically modified cell of any one of more of the cells of any one of the alternatives herein or the composition of any one of the alternatives is provided. The composition comprising the genetically engineered cell of any one or more of the cells of any one of the alternatives herein and a pharmaceutical excipient is provided. The genetically engineered cell for the expression of FOXP3 can be manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the genetically engineered cell for the expression of FOXP3 comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the subject is given a combination therapy, which the subject is administered anti-rejection drugs in combination with the engineered cells. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the subject is monitored for changes in FOXp3+Treg-phenotype cell populations in vivo during the course of treatment. In some alternatives, the subject is selected to receive another administration of engineered cells. In some alternatives, the subject in need is selected to receive an anti-rejection therapy or anti-inflammatory therapy. In some alternatives, the method further comprises determining that the engineered cells are in the subject in need by sequencing for the genetically engineered cell to determine that the engineered cell is maintained, increased or decreased in the subject. In some alternatives, the subject is given a combination therapy, which the subject is administered anti-rejection drugs or anti-inflammatory drugs in combination with the engineered cells. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the anti-inflammatory drugs comprise Tysabri®, steroids, ammunosuppressants, NSAID's, immunoglobulins, paracetramol, celecoxib, indomethacin or diclofenac. In some alternatives, the subject is monitored for changes in the engineered T cells expressing FOXp3+, and the populations of engineered cells that express a Treg phenotype or pathogenic T- or B-cells populations in vivo before, during and/or after the course of treatment, inhibition, or amelioration. In some alternatives, the subject is selected to receive another administration of engineered cells depending to the first response to treatment, inhibition, or amelioration. In some alternatives, the subject is administered another dose of cells within 1 week, 2 weeks or one month from the initial dose. In some alternatives, of the methods of treatments described herein, the methods further comprise monitoring the subject to determine if the engineered cells are maintained, increased or decreased before, during and/or after treatment. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

In some alternatives, a method of treating, inhibiting, or ameliorating side effects of organ transplantation in a subject, such as organ rejection is provided, the method comprising: administering to the subject the genetically modified cell of any one of more of the cells of any one of the alternatives herein or the composition of any one of the alternatives is provided. The composition comprising the genetically engineered cell of any one or more of the cells of any one of the alternatives herein and a pharmaceutical excipient is provided. The genetically engineered cell for the expression of FOXP3 can be manufactured by the method of any one of the alternatives herein is provided. The method of making a genetically engineered cell is provided, the method comprising providing a cell, wherein the cell comprises a first nucleotide sequence, wherein the first nucleotide sequence comprises a coding strand, the coding strand comprising one or more regulatory elements; and a FOXP3 gene or portion thereof; providing a second nucleotide sequence encoding a nuclease or providing a protein nuclease; and introducing the second oligonucleotide or protein nuclease into the cell for a gene editing process. In some alternatives, the gene editing process is a gene knock-in process for insertion of a heterologous promoter into the first nucleotide sequence. In some alternatives, the coding strand comprises a first coding exon. In some alternatives, the first nucleotide sequence comprises a targeted locus. In some alternatives, the targeted locus comprises a natural coding exon or the first coding exon. In some alternatives, completion of the gene editing process results in a first coding exon in the targeting locus following the gene editing process. In some alternatives, the targeted locus is within 10, 20, 30, 40, 50, 60, 70, 80, 90, 100 or 110 base pairs upstream of the first coding exon or any number of base pairs in between a range defined by any two aforementioned values. In some alternatives, the gene editing process further comprises creation of a synthetic first coding exon. In some alternatives, the nuclease is Cas9, a zinc-finger nuclease or TALEN. In some alternatives, the heterologous promoter is a constitutive promoter. In some alternatives, the heterologous promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the method further comprises insertion of a heterologous enhancer domain (e.g., TCRa enhancer) into the first nucleotide sequence wherein the enhancer domain is upstream or downstream from the one or more regulatory sequences. In some alternatives, the method further comprises insertion of a heterologous transcriptional activation domain into the first nucleotide sequence. In some alternatives, the method further comprises insertion of a ubiquitous chromatin opening element (UCOE) into the first nucleotide sequence. In some alternatives, the heterologous promoter is inserted upstream from the first coding exon on the coding strand during the genetic modification, or the genetic modification results in a synthetic first coding exon that is created through completion of the gene editing process, wherein the heterologous promoter is upstream from the synthetic first coding exon. In some alternatives, the heterologous promoter is inserted downstream from the one or more regulatory elements on the coding strand. In some alternatives, the method further comprises genetically modifying the one or more regulatory elements. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the genetically engineered cell for the expression of FOXP3 comprises a nucleic acid, wherein the nucleic acid comprises a coding strand comprising one or more regulatory elements and a heterologous promoter operably linked to a FOXP3 gene, wherein the FOXP3 gene comprises a first coding exon. In some alternatives, the heterologous promoter is a constitutive promoter. In some alternatives, the constitutive promoter is an EF1 alpha promoter, a PGK promoter, or an MND promoter. In some alternatives, the heterologous promoter is a weak promoter (e.g., a promoter that generates less expression than the endogenous promoter and/or a constitutive promoter). In some alternatives, the heterologous promoter is an inducible promoter. In some alternatives, the inducible promoter is inducible by a drug or a steroid. In some alternatives, the heterologous promoter is inserted upstream from the first coding exon. In some alternatives, the nucleic acid further comprises a heterologous transcriptional enhancer domain. In some alternatives, the nucleic acid further comprises a heterologous transcriptional activation domain. In some alternatives, the nucleic acid further comprises a ubiquitous chromatin opening element (UCOE). In some alternatives, the heterologous promoter is inserted downstream from the one or more regulatory elements on the coding strand. In some alternatives, the one or more regulatory elements are genetically modified. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the subject is given a combination therapy, which the subject is administered anti-rejection drugs in combination with the engineered cells. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the subject is monitored for changes in FOXp3+Treg-phenotype cell populations in vivo during the course of treatment. In some alternatives, the subject is selected to receive another administration of engineered cells. In some alternatives, the subject in need is selected to receive an anti-rejection therapy or anti-inflammatory therapy. In some alternatives, the method further comprises determining that the engineered cells are in the subject in need by sequencing for the genetically engineered cell to determine that the engineered cell is maintained, increased or decreased in the subject. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the anti-inflammatory drugs comprise Tysabri®, steroids, ammunosuppressants, NSAID's, immunoglobulins, paracetramol, celecoxib, indomethacin or diclofenac. In some alternatives, the subject is monitored for changes in the engineered T cells expressing FOXp3+, and the populations of engineered cells that express a Treg phenotype or pathogenic T- or B-cells populations in vivo before, during and/or after the course of treatment, inhibition, or amelioration. In some alternatives, the subject is selected to receive another administration of engineered cells depending to the first response to treatment, inhibition, or amelioration. In some alternatives, the subject is administered another dose of cells within 1 week, 2 weeks or one month from the initial dose. In some alternatives, of the methods of treatments described herein, the methods further comprise monitoring the subject to determine if the engineered cells are maintained, increased or decreased before, during and/or after receiving the first administration of cells. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

In some alternatives, a method of treating, inhibiting, or ameliorating an autoimmune disorder in a subject is provided, the method comprising withdrawing cells from the subject in need, wherein the cells comprise a first nucleotide sequence, wherein the first nucleotide sequence comprises a coding strand, the coding strand comprising one or more regulatory elements, a FOXP3 gene or portion thereof, wherein the FOXP3 gene or portion thereof comprises a first coding exon, providing a second nucleotide sequence encoding a nuclease or providing a protein nuclease, introducing the second nucleotide sequence or protein nuclease into the cell for genetic modification, wherein the genetic modification is a gene knock-in process for insertion of a promoter into the first nucleotide sequence; and introducing the cell into the subject for treatment, inhibition, or amelioration. In some alternatives, the autoimmune disease is rheumatoid arthritis, diabetes, inflammatory bowel disease, IPEX, immune dysregulation, polyendocrinopathy, enteropathy, X-linked (IPEX) syndrome, Crohn's disease, multiple sclerosis, idiopathic or systemic lupus erythematosus. In some alternatives, the subject is identified or selected to receive therapy for an autoimmune disease. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the subject is given a combination therapy, which the subject is administered drugs for ameliorating the autoimmune disease symptoms in combination with the engineered cells. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the subject is monitored for changes in FOXp3+Treg-phenotype cell populations in vivo during the course of treatment. In some alternatives, the subject is selected to receive another administration of engineered cells. In some alternatives, the subject in need is selected to receive an anti-rejection therapy or anti-inflammatory therapy. In some alternatives, the method further comprises determining that the engineered cells are in the subject in need by sequencing for the genetically engineered cell to determine that the engineered cell is maintained, increased or decreased in the subject. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the anti-inflammatory drugs comprise Tysabri®, steroids, ammunosuppressants, NSAID's, immunoglobulins, paracetramol, celecoxib, indomethacin or diclofenac. In some alternatives, the subject is monitored for changes in the engineered T cells expressing FOXp3+, and the populations of engineered cells that express a Treg phenotype or pathogenic T- or B-cells populations in vivo before, during and/or after the course of treatment. In some alternatives, the subject is selected to receive another administration of engineered cells depending to the first response to treatment. In some alternatives, the subject is administered another dose of cells within 1 week, 2 weeks or one month from the initial dose. In some alternatives, of the methods of treatments described herein, the methods further comprise monitoring the subject to determine if the engineered cells are maintained, increased or decreased before, during and/or after treatment. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

In some alternatives, a method of treating, inhibiting, or ameliorating side effects of organ transplantation in a subject is provided, the method comprising withdrawing cells from the subject in need, wherein the cells comprise a first nucleotide sequence, wherein the first nucleotide sequence comprises a coding strand, the coding strand comprising one or more regulatory elements, a FOXP3 gene or portion thereof, wherein the FOXP3 gene or portion thereof comprises a first coding exon, providing a second nucleotide sequence encoding a nuclease or providing a protein nuclease, introducing the second nucleotide sequence or protein nuclease into the cell for genetic modification, wherein the genetic modification is a gene knock-in process for insertion of a promoter into the first nucleotide sequence; and introducing the cell into the subject for treatment. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the subject is given a combination therapy, which the subject is administered anti-rejection drugs in combination with the engineered cells. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the subject is monitored for changes in FOXp3+Treg-phenotype cell populations in vivo during the course of treatment, inhibition, or amelioration. In some alternatives, the subject is selected to receive another administration of engineered cells. In some alternatives, the subject in need is selected to receive an anti-rejection therapy or anti-inflammatory therapy. In some alternatives, the method further comprises determining that the engineered cells are in the subject in need by sequencing for the genetically engineered cell to determine that the engineered cell is maintained, increased or decreased in the subject. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the anti-inflammatory drugs comprise Tysabri®, steroids, ammunosuppressants, NSAID's, immunoglobulins, paracetramol, celecoxib, indomethacin or diclofenac. In some alternatives, the subject is monitored for changes in the engineered T cells expressing FOXp3+, and the populations of engineered cells that express a Treg phenotype or pathogenic T- or B-cells populations in vivo before, during and/or after the course of treatment, inhibition, or amelioration. In some alternatives, the subject is selected to receive another administration of engineered cells depending to the first response to treatment. In some alternatives, the subject is administered another dose of cells within 1 week, 2 weeks or one month from the initial dose. In some alternatives, of the methods of treatments, inhibitions, or ameliorations described herein, the methods further comprise monitoring the subject to determine if the engineered cells are maintained, increased or decreased before, during and/or after treatment. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

In some alternatives, a method of treating, inhibiting, or ameliorating side effects of organ transplantation in a subject, such as organ rejection is provided, the method comprising withdrawing cells from the subject in need, wherein the cells comprise a first nucleotide sequence, wherein the first nucleotide sequence comprises a coding strand, the coding strand comprising one or more regulatory elements, a FOXP3 gene or portion thereof, wherein the FOXP3 gene or portion thereof comprises a first coding exon, providing a second nucleotide sequence encoding a nuclease or providing a protein nuclease, introducing the second nucleotide sequence or protein nuclease into the cell for genetic modification, wherein the genetic modification is a gene knock-in process for insertion of a promoter into the first nucleotide sequence and introducing the cell into the subject for treatment. In some alternatives, the cell is a precursor stem cell. In some alternatives, the cell is a hematopoietic stem cell. In some alternatives, the cell is a CD4+ expressing cell. In some alternatives, the cell is a CD8+ expressing cell. In some alternatives, the cell is a T-regulatory cell. In some alternatives, the subject is given a combination therapy, which the subject is administered anti-rejection drugs in combination with the engineered cells. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the subject is monitored for changes in FOXp3+Treg-phenotype cell populations in vivo during the course of treatment. In some alternatives, the subject is selected to receive another administration of engineered cells. In some alternatives, the subject in need is selected to receive an anti-rejection therapy or anti-inflammatory therapy. In some alternatives, the method further comprises determining that the engineered cells are in the subject in need by sequencing for the genetically engineered cell to determine that the engineered cell is maintained, increased or decreased in the subject. In some alternatives, the subject is selected to receive anti-rejection medications. In some alternatives, the anti-rejection medications comprise Prednisone, Imuran (azathioprine), Collect (mycophenolate mofetil, or MMF), Myfortic (mycophemolic acid), Rapamune (sirolimus), Neoral (cyclosporine), or Prograf (tacrolimus). In some alternatives, the anti-inflammatory drugs comprise Tysabri®, steroids, ammunosuppressants, NSAID's, immunoglobulins, paracetramol, celecoxib, indomethacin or diclofenac. In some alternatives, the subject is monitored for changes in the engineered T cells expressing FOXp3+, and the populations of engineered cells that express a Treg phenotype or pathogenic T- or B-cells populations in vivo before, during and/or after the course of treatment, inhibition, or amelioration. In some alternatives, the subject is selected to receive another administration of engineered cells depending on the first response to the first administration of cells. In some alternatives, the subject is administered another dose of cells within 1 week, 2 weeks or one month from the initial dose. In some alternatives, of the methods of treatments described herein, the methods further comprise monitoring the subject to determine if the engineered cells are maintained, increased or decreased before, during and/or after receiving the cells. In some alternatives, a sample of cells is withdrawn from the subject to detect the engineered cells and to determine if the engineered cell is maintained, increased or decreased. In some alternatives, another administration of engineered cells is given to the subject in need if the engineered cells have decreased in the subject. In some alternatives, the subject is refractory to standard therapies for autoimmune disease or standard therapies for anti-inflammatory therapies. In some alternatives, the subject is refractory to standard anti-rejection medications or standard anti-rejection therapies. As such, in some alternatives, the subject is selected to receive genetically engineered cells that express FOXP3.

What is claimed is:
1. A method of editing a genome in a cell, the method comprising introducing into the cell:
   (a) a first nucleic acid comprising a heterologous promoter; and
   (b) a nuclease or a second nucleic acid encoding the nuclease, wherein the nuclease is capable of cleaving a targeted locus within or upstream from the first coding exon of a FOXP3 gene in the cell genome, wherein the heterologous promoter is inserted into the cell genome downstream from a Treg-specific demethylated region (TSDR) of the FOXP3 gene, and is operably linked to the FOXP3 gene, thereby producing an engineered cell.

2. The method of claim 1, wherein the heterologous promoter is a constitutive promoter.

3. The method of claim 2, wherein the constitutive promoter is an EF1-α promoter, a PGK promoter, or an MND promoter.

4. The method of claim 1, wherein the heterologous promoter is an inducible promoter.

5. The method of claim 1, wherein the targeted locus is within the first coding exon of the FOXP3 gene.

6. The method of claim 1, wherein the nuclease is a Cas9 nuclease, a zinc-finger nuclease, or a TALEN.

7. The method of claim 1, wherein the cell is a precursor stem cell, a hematopoietic stem cell, a CD4+ T cell, a CD8+ T cell, or a T regulatory (Treg) cell.

8. The method of claim 1, wherein the cell is a CD4+ T cell and the heterologous regulatory element is a constitutive promoter.

9. The method of claim 8, wherein the engineered cell has a T regulatory (Treg) cell phenotype.

10. The method of claim 1, wherein the targeted locus is within 110 base pairs upstream of the first coding exon.

11. The method of claim 1, wherein inserting the heterologous promoter into the genome creates a synthetic first coding exon, such that the genome lacks a natural first coding exon following insertion of the heterologous promoter.

12. The method of claim 11, wherein inserting the heterologous promoter is upstream from the synthetic first coding exon.

13. The method of claim 1, wherein the heterologous promoter is inserted upstream from a natural first coding exon of the FOXP3 gene.

14. The method of claim 1, further comprising inserting a heterologous enhancer domain into the cell genome, wherein the heterologous enhancer domain is inserted upstream or downstream from one or more regulatory elements of the FOXP3 gene.

15. The method of claim 1, further comprising inserting a heterologous transcriptional activation domain into the cell genome.

16. The method of claim 1, further comprising inserting a ubiquitous chromatin opening element (UCOE) into the cell genome.

17. The method of claim 1, wherein the cell expresses a chimeric antigen receptor (CAR).

18. The method of claim 1, wherein the cell expresses a T cell receptor (TCR).

19. The method of claim 3, wherein the constitutive promoter is an MND promoter.

* * * * *

UNITED STATES PATENT AND TRADEMARK OFFICE
CERTIFICATE OF CORRECTION

PATENT NO. : 11,712,454 B2
APPLICATION NO. : 16/345622
DATED : August 1, 2023
INVENTOR(S) : Andrew M. Scharenberg It is certified that error appears in the above-identified patent and that said Letters Patent is hereby corrected as shown below:

On the Title Page

Column 2 (Other Publications), Line 3, delete "(2012))" and insert -- (2012) --.

Page 2, Column 1 (Other Publications), Line 28, delete "glomerulopephritis," and insert -- glomerulonephritis, --.

In the Drawings

Sheet 2 of 26, (FIG. 2), Line 6, delete "Adena-Associated Viurs" and insert -- Adeno-Associated Virus --.

In the Specification

Column 22, Line 8, delete "mycophemolic" and insert -- mycophenolic --.

Column 22, Line 19, delete "mellitis" and insert -- mellitus --.

Column 26, Line 49, delete "cells" and insert -- cells. --.

Column 28, Line 59, delete "GVHD" and insert -- GvHD --.

Column 37, Line 45, delete "mycophemolic" and insert -- mycophenolic --.

Column 37, Line 48, delete "ammunosuppressants," and insert -- immunosuppressants, --.

Column 37, Line 49, delete "paracetramol," and insert -- paracetamol, --.

Column 43, Line 6, delete "exon In" and insert -- exon. In --.

Signed and Sealed this
Tenth Day of October, 2023

Katherine Kelly Vidal
*Director of the United States Patent and Trademark Office*

CERTIFICATE OF CORRECTION (continued)
U.S. Pat. No. 11,712,454 B2

Column 43, Line 63, delete "exon In" and insert -- exon. In --.

Column 50, Line 27, delete "mycophemolic" and insert -- mycophenolic --.

Column 50, Line 30, delete "ammunosuppressants," and insert -- immunosuppressants, --.

Column 50, Line 30-31, delete "paracetramol," and insert -- paracetamol, --.

Column 52, Line 22, delete "mycophemolic" and insert -- mycophenolic --.

Column 52, Line 41-42, delete "mycophemolic" and insert -- mycophenolic --.

Column 52, Line 45, delete "ammunosuppressants," and insert -- immunosuppressants, --.

Column 52, Line 45-46, delete "paracetramol," and insert -- paracetamol, --.

Column 54, Line 51, delete "mycophemolic" and insert -- mycophenolic --.

Column 54, Line 67, delete "mycophemolic" and insert -- mycophenolic --.

Column 55, Line 3, delete "ammunosuppressants," and insert -- immunosuppressants, --.

Column 55, Line 4, delete "paracetramol," and insert -- paracetamol, --.

Column 55, Line 66, delete "mycophemolic" and insert -- mycophenolic --.

Column 56, Line 15, delete "mycophemolic" and insert -- mycophenolic --.

Column 56, Line 18, delete "ammunosuppressants," and insert -- immunosuppressants, --.

Column 56, Line 19, delete "paracetramol," and insert -- paracetamol, --.

Column 57, Line 5, delete "mycophemolic" and insert -- mycophenolic --.

Column 57, Line 21-22, delete "mycophemolic" and insert -- mycophenolic --.

Column 57, Line 25, delete "ammunosuppressants," and insert -- immunosuppressants, --.

Column 57, Line 25-26, delete "paracetramol," and insert -- paracetamol, --.

Column 58, Line 13, delete "mycophemolic" and insert -- mycophenolic --.

Column 58, Line 29, delete "mycophemolic" and insert -- mycophenolic --.

CERTIFICATE OF CORRECTION (continued)
U.S. Pat. No. 11,712,454 B2

Column 58, Line 32, delete "ammunosuppressants," and insert -- immunosuppressants, --.

Column 58, Line 33, delete "paracetramol," and insert -- paracetamol, --.